(12) United States Patent
Albahri

(10) Patent No.: US 9,201,053 B2
(45) Date of Patent: Dec. 1, 2015

(54) METHOD FOR MEASURING THE PROPERTIES OF PETROLEUM FUELS BY DISTILLATION

(71) Applicant: KUWAIT UNIVERSITY, Safat (KW)

(72) Inventor: Tareq Abduljalil Albahri, Laber Al-Ali (KW)

(73) Assignee: Kuwait University, Safat (KW)

( * ) Notice: Subject to any disclaimer, the term of this patent is extended or adjusted under 35 U.S.C. 154(b) by 74 days.

(21) Appl. No.: 14/105,467

(22) Filed: Dec. 13, 2013

(65) Prior Publication Data

US 2014/0107941 A1   Apr. 17, 2014

Related U.S. Application Data

(60) Division of application No. 12/662,376, filed on Apr. 14, 2010, now Pat. No. 8,645,079, and a continuation-in-part of application No. 11/216,120, filed on Sep. 1, 2005, now abandoned.

(51) Int. Cl.
| | |
|---|---|
| G01N 33/22 | (2006.01) |
| G01N 25/14 | (2006.01) |
| G01N 33/28 | (2006.01) |
| G06F 19/00 | (2011.01) |
| G01N 33/00 | (2006.01) |

(52) U.S. Cl.
CPC .............. *G01N 33/225* (2013.01); *G01N 25/14* (2013.01); *G01N 33/0004* (2013.01); *G01N 33/28* (2013.01); *G06F 19/704* (2013.01); *G06F 19/707* (2013.01)

(58) Field of Classification Search
USPC .......................................................... 702/24
See application file for complete search history.

(56) References Cited

U.S. PATENT DOCUMENTS

| | | | |
|---|---|---|---|
| 2,375,478 A | | 5/1945 | Lake |
| 3,835,034 A | * | 9/1974 | Barnett ......................... 208/139 |
| 3,839,194 A | * | 10/1974 | Sinfelt et al. .................. 208/139 |
| 4,332,776 A | * | 6/1982 | Stana .............................. 423/10 |
| 4,800,279 A | | 1/1989 | Hieftje et al. |
| 4,963,745 A | | 10/1990 | Maggard |
| 5,121,337 A | | 6/1992 | Brown |
| 5,139,621 A | | 8/1992 | Alexander et al. |
| 5,145,785 A | | 9/1992 | Maggard et al. |
| 5,218,529 A | | 6/1993 | Meyer et al. |
| 5,225,679 A | | 7/1993 | Clarke et al. |
| 5,349,188 A | | 9/1994 | Maggard |
| 5,349,189 A | | 9/1994 | Maggard |
| 5,360,972 A | | 11/1994 | DiFoggio et al. |
| 5,362,965 A | | 11/1994 | Maggard |

(Continued)

OTHER PUBLICATIONS

T. Albahri, "Enhanced Method for Predicting the Properties of Petroleum Fractions", ACS Symposium Series, American Chemical Society, Division of fuel chemistry preprints: Philadelphia, PA, Aug. 22, 2004, vol. 49(2), p. 925-926.

(Continued)

*Primary Examiner* — Tung S Lau
(74) *Attorney, Agent, or Firm* — Richard C. Litman

(57) ABSTRACT

The method for measuring the properties of petroleum fuels by distillation relates to a measuring method for predicting the property values of complex hydrocarbon fuels, such as the property values of gasoline, by distillation. Compensation of boiling point distribution measurements used for the prediction of physical properties of hydrocarbons is further performed.

1 Claim, 20 Drawing Sheets

(56) References Cited

U.S. PATENT DOCUMENTS

| | | |
|---|---|---|
| 5,412,581 A | 5/1995 | Tackett |
| 5,424,959 A | 6/1995 | Reyes et al. |
| 5,446,681 A | 8/1995 | Gethner et al. |
| 5,452,232 A | 9/1995 | Espinosa et al. |
| 5,699,269 A | 12/1997 | Ashe et al. |
| 5,705,139 A * | 1/1998 | Stiller et al. ............. 423/445 R |
| 6,275,775 B1 | 8/2001 | Baco et al. |
| 6,392,115 B1 | 5/2002 | Gasem et al. |
| 6,402,897 B1 | 6/2002 | Gunn |
| 6,558,515 B1 * | 5/2003 | Steacy .............................. 203/1 |
| 6,581,443 B2 | 6/2003 | Abaev et al. |
| 6,617,483 B1 | 9/2003 | McKim et al. |
| 6,711,532 B1 | 3/2004 | Spieksma |
| 2006/0006098 A1 | 1/2006 | Espinoza et al. |

OTHER PUBLICATIONS

T. Albahri, "Molecularly Explicit Characterization Model (MECM) for Light Petroleum Fractions", Ind. Eng. Chem. Res., 2005, 44, 9286-9298.

* cited by examiner

- Propane
- n-butane
- n-pentane
- 2,2-dimethyl butane (neohexane)
- 2-methyle pentane
- N-hexane
- 2,2-dimethylpentane
- 2,4-dimethylpentane
- 2,2,3-trimethylbutane (Triptane)
- 1,1-dimethylpentane
- 2-methylhexane
- 1,2-dimethyl cyclopentane-trans
- trans-1,3-dimethylcyclopentane
- N-heptane
- 2,2-dimethylhexane
- 2,4-dimethylhexane
- Toluene
- 2,3-dimethylhexane
- 2-methyheptane
- 4-methylheptane
- 3-ethylhexane
- cis-1,3-ethylmethylcyclopentane
- trans-1,3-ethylmethylcyclopentane
- N-octane

- isobutane
- 2-methyl butane (isopentane)
- Cyclopentane
- 2,3-dimethyl butane
- 3-methyl pentane
- methylcyclopentane
- Benzene
- Cyclohexane
- 3,3-dimethylpentane
- 2,3-dimethylpentane
- cis-1,3-dimethylcyclopentane
- 3-methylhexane
- 3-ethylpentane
- Ethylcyclopentane
- 2,5-dimethylhexane
- 2,2,3-trimethylpentane
- 3,3-dimethylhexane
- 2-methyl-3-ethylpentane
- 3,4-dimethylhexane
- 3-methyl-3-ethylpentane
- 3-methylheptane
- trans-1,2-ethylmethylcyclopentane
- 2,2,5-trimethylhexane

*Fig. 6B*

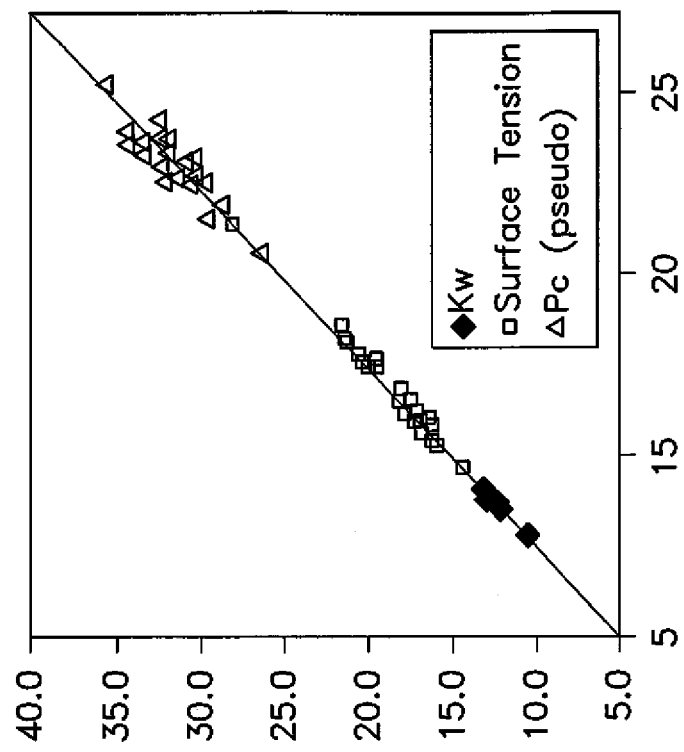
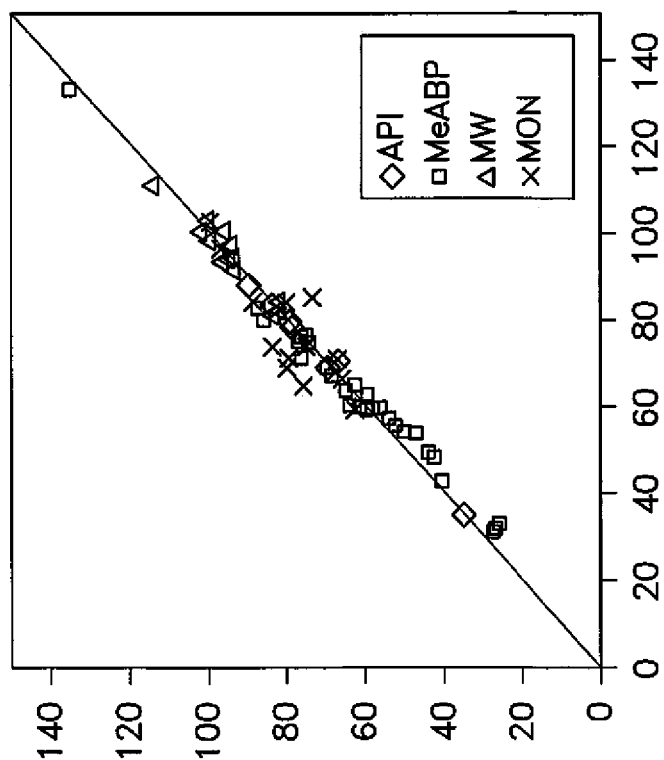
Fig. 7B
Fig. 7A

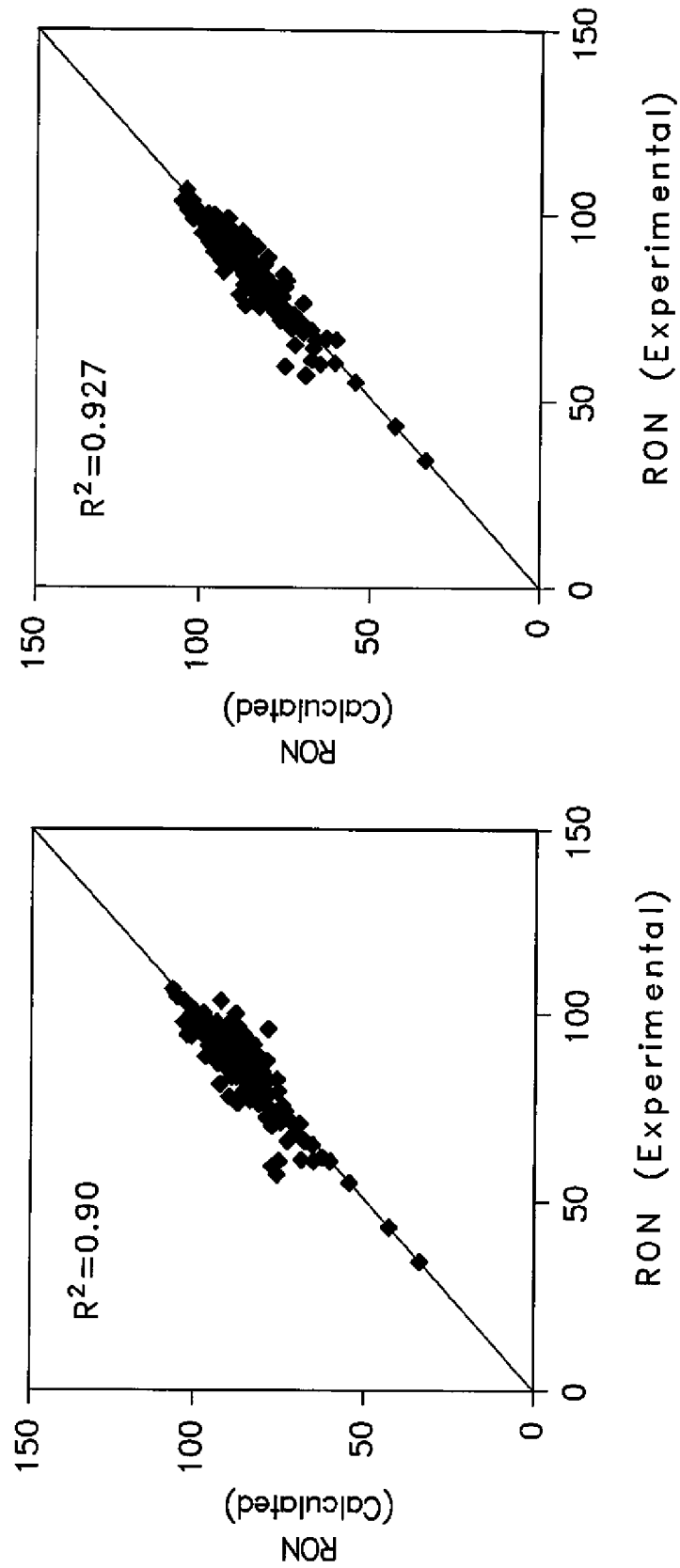

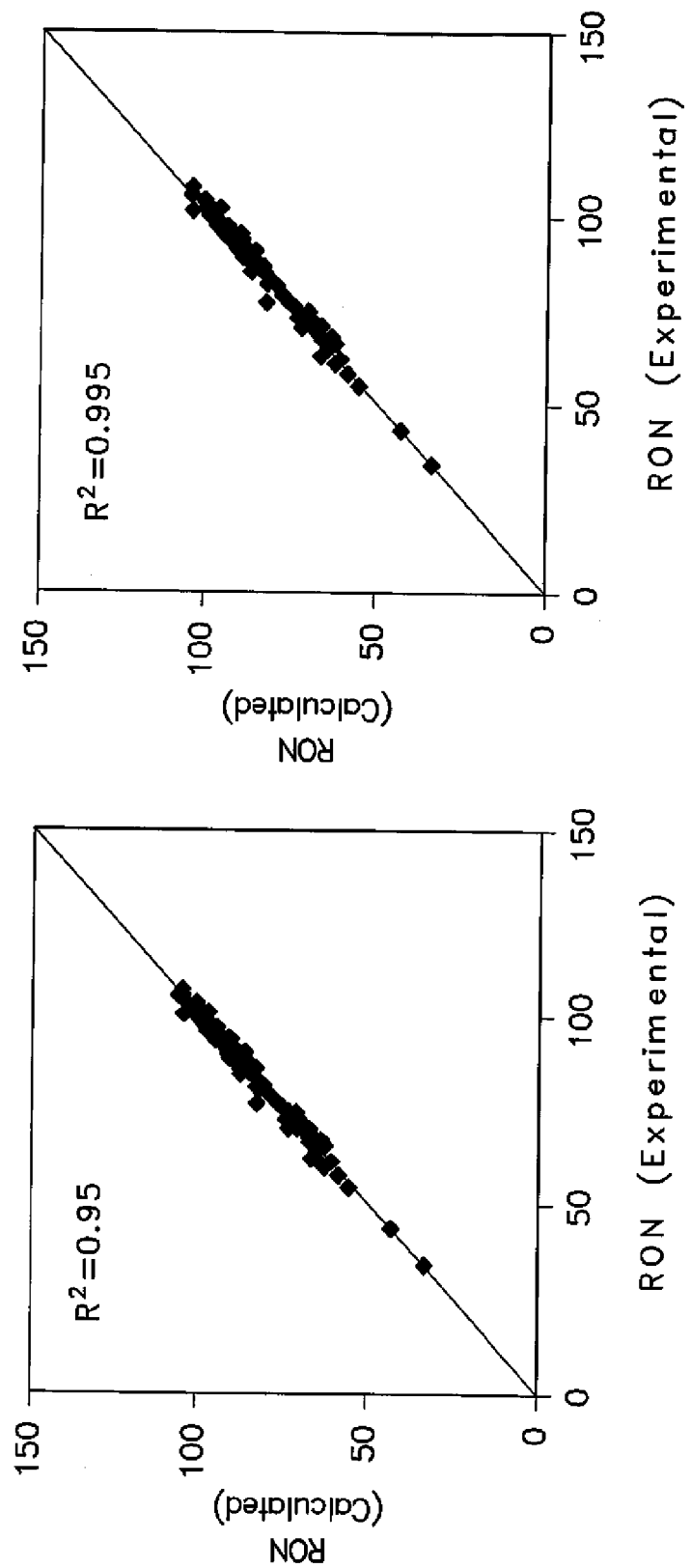

US 9,201,053 B2

METHOD FOR MEASURING THE PROPERTIES OF PETROLEUM FUELS BY DISTILLATION

CROSS-REFERENCE TO RELATED APPLICATION

This application is a divisional of U.S. patent application Ser. No. 12/662,376, filed on Apr. 14, 2010, now U.S. Pat. No. 8,645,079; which is a continuation-in-part of U.S. patent application Ser. No. 11/216,120, filed on Sep. 1, 2005, now abandoned; the contents of these applications are herein incorporated by reference in their entirety.

BACKGROUND OF THE INVENTION

1. Field of the Invention

The present invention relates to material analysis, and particularly to a measuring method for predicting the property values of complex hydrocarbon fuels, such as the property values of gasoline by distillation. More particularly, the present invention relates to compensation of boiling point distribution measurements used for the prediction of physical properties of hydrocarbons.

2. Description of the Related Art

Petroleum products, such as gasoline, are typically formulated as blends consisting of thousands of chemical compounds. For a wide variety of applications, it is desirable to be able to identify and quantify each of these components. These products are generally identified and classified based on some of the bulk properties, such as, for example, the range of distillation, density, and the cetane number, viscosity, pour point, API gravity and the like. These data are useful both during production of such fuels at the refinery and also during delivery of such fuels to the end-user. In either case, with these data, the producer, for production control purposes, or the consumer, to meet engine requirements or for comparative purposes, can assess the quality or value of the particular product. It is therefore of great interest to be able to ascertain, with specificity, the properties of hydrocarbon-based fuels.

Many characterizing properties or attributes, such as Reid vapor pressure, viscosity, refractive index, hydrogen-to-carbon (H/C) content, paraffin, naphthene and aromatic (PNA) content, aniline point, octane number, freezing point, cloud point, smoke point, diesel index, refractive index, cetane index, and the like are generally measured for a crude oil or only certain of its fractions according to well-specified ASTM tests.

Detailed characterization of petroleum fuels entails the use of sophisticated analytical equipment, such as gas chromatography (GC) and nuclear magnetic resonance (NMR). Although it is possible to obtain detailed molecular and structural composition of petroleum fractions using GC-MS and NMR techniques on the order of a few days, these extensive experimental programs can be complex, expensive and overly consuming in terms of both time and computing power. Because of the issues involved, these analytical methods do not find wide acceptance in daily refinery operations.

Accurate characterization of petroleum fuels is an important step in the application of kinetic and thermodynamic calculations for the design, operation, and simulation of petroleum refining processes. An insufficient description of heavier hydrocarbons (e.g., pentane and heavier; $C_5+$) reduces the accuracy of predictions. Unfortunately, complete experimental data on the $C_5+$ hydrocarbon fraction are seldom available. Ideally, fuel properties are determined experimentally in the laboratory on actual fluid samples taken from the process under study. Because of the expense of the experimental determination of such data, there is interest in their accurate prediction.

In order to speed up the execution of real-time simulation, it would desirable to be able to utilize a series of simplified correlations for the evaluation of physical properties of petroleum fractions. Using available data, present methods require as input parameters the fuel global properties, such as the average boiling point, the specific gravity and some characterization factors. Unfortunately, with these input requirements, the models are not suitable for incorporation into the latest generation of molecularly explicit simulation models. In addition, wide boiling range fractions are mixtures of a large number of hydrocarbon compounds, the types of which vary along the distillation curve, therefore a single value for boiling point or specific gravity does not characterize the fraction very well. Moreover, as many existing correlations are based on properties of pure compounds, errors in predicted values from the correlations increase significantly when the methods are applied to mixtures.

Distillation curves provide a breadth of information about the crude oil or the petroleum fuel. In certain respects, the boiling point distribution is representative of the composition of the petroleum fraction. Therefore, in principle, by determining the presence and volume percent of the components in a conventional hydrocarbon fuel solution, the overall physical properties can be determined.

There are many types of standard distillation tests that determine the boiling point distribution of petroleum fuels, the inter-conversion between which is well documented. Some of the more common standard test methods for distillation of petroleum products include: ASTM D86-96, which is performed under atmospheric pressure and is used for determining the boiling point distribution of light petroleum fractions, such as naphtha, kerosene, diesel, and light gas oil; micro-distillation; molecular distillation; fractional distillation (typically using a spinning band still); ASTM D5236 distillation (typically using a pot still); D1160 (for heavy petroleum fractions); ASTM D3710 (simulated distillation, which is also known as the GC SimDist method, and uses gas chromatography to determine the true boiling point, or TBP, of gasoline); ASTM D2887 (GC SimDist to determine the TBP of petroleum fraction other than gasoline); ASTM D2892 (also known as 15/5 distillation, which produces simulated TBP of petroleum fuels using a distillation column with 15 theoretical plates and a reflux ratio of 5); ASTM D5236 Distillation (also known as the vacuum pot still method, and is used for heavy hydrocarbon mixtures); ASTM D5307 (SimDist for determining TBP of crude oil); ASTM D6352-98; and Hemple analysis for the distillation of a large volume of fuel samples providing further detailed analysis of the produced distilled cuts. ASTM D86-96 and D1160 may be combined together for determining the boiling point distribution of wide boiling range materials, such as crude oils.

In a distillation device operated according to the ASTM D86 standard test method, for example, a 100 ml petroleum sample, placed in a flask, is heated at a regulated rate, so that a uniform average rate of condensation in mL/min is maintained. This rate varies from zero to five volume % recovered, from 5 to 10 volume % recovered, and so on. When the first drop appears at the lower end of the condenser tube, the thermometer reading (vapor temperature) is recorded as the initial boiling point (IBP). Temperature readings are recorded at several volume % distilled (as shown in Table 1 below), up to the final boiling point (FBP) and heating is discontinued.

After the flask has cooled, the volume of remaining liquid is measured and recorded as the recovery. For heavy fractions, heating is discontinued when the decomposition point is observed, and the vapor reaches a maximum temperature and then starts declining before the end point. The volume increments for the reported boiling point distribution by the ASTM distillation apparatus is user-selected, and Table 1 illustrates one such example:

TABLE 1

Data output from ASTM D86 distillation test

| Vol % | T (° F.) |
|---|---|
| 0 | IBP |
| 10 | $T_{10\%}$ |
| 30 | $T_{30\%}$ |
| 50 | $T_{50\%}$ |
| 70 | $T_{70\%}$ |
| 90 | $T_{90\%}$ |
| 100 | FBP |
| Recovery | ~98% |

Traditionally, the analytical methods that relate to determining petroleum properties in hydrocarbons take a long time to carry out and are thus very time-consuming. In the laboratory, the properties are measured using numerous and varying types of analytical and physical test equipment, with skilled personnel being required to perform the testing. For each experimentally determined property, there is at least one apparatus, thus for 30 properties there is a need for 30 separate experimental apparatuses. Such equipment is very expensive, requires frequent maintenance, and also requires the availability of many samples of the fuel, along with taking between several minutes and several hours per sample to run the tests.

Thus, a system and method for measuring the properties of petroleum fuels by distillation solving the aforementioned problems is desired.

SUMMARY OF THE INVENTION

The present invention relates to material analysis, and particularly to a measuring method for predicting the property values of complex hydrocarbon fuels, such as the property values of gasoline by distillation. More particularly, the present invention relates to compensation of boiling point distribution measurements used for the prediction of physical properties of hydrocarbons.

The method for measuring the properties of petroleum fuels by distillation begins with the storing of an initial data set of properties associated with a selected light petroleum fraction in computer readable memory. The initial data set of properties includes API gravity, RVP, PNA content and true boiling point. The values for the API gravity, the RVP and the PNA content may be estimated based upon the true boiling point, which is found experimentally through ASTM D86 distillation. Next, a molecular ensemble is generated, with the molecular ensemble including a plurality of molecular species, each with a known pure component API gravity, RVP, PNA content and true boiling point. The pure component data set is stored in the computer readable memory.

At least one mixing rule is applied to the pure component data set to calculate a concentration of light components of the selected light petroleum fraction based upon the pure component API gravity and RVP. Following this, the at least one mixing rule is further applied to the pure component data set to calculate a concentration of heavier components of the selected light petroleum fraction based upon the pure component PNA content and true boiling point.

The API gravity, the RVP, the PNA content and the true boiling point of the initial data set is then compared with the pure component API gravity, RVP, PNA content and true boiling point to form a set of comparison data. This set of comparison data is optimized, with the optimization including application of an objective function. Preferably, a distribution of the molecular ensemble in terms of volume fractions is generated by minimizing the objective function S as:

$$S = \sum_{j=1}^{n}((Tb_j - T'b_j) \times W_o \times 100/Tb_j)^2 + ((PNA - PNA') \times W_1 \times 100/PNA)^2,$$

wherein j is an index number of the molecule and n represents the total number of molecules, PNA represents the paraffin, naphthene, and aromatic content for the petroleum fraction, PNA' is the paraffin, naphthene, and aromatic content for the petroleum fraction calculated from aggregating pure components in the molecular ensemble using the at least one mixing rule, T'$b_j$ is the boiling point of pure component j, $Tb_j$ is the boiling point value on a petroleum fractions true boiling point curve corresponding to component j, $W_o$ is a weighting factor for the boiling points and $W_1$ is a weighting factor for the PNA fractional composition.

Alternatively, S may be minimized as:

$$S = \sum_{j=1}^{n}((Tb_j - T'b_j) \times W_o \times 100/Tb_j)^2 + ((P\% - P\%') \times W_1 \times 100/P\%)^2 + $$
$$((N\% - N\%') \times W_1 \times 100/N\%)^2 + ((A\% - A'\%) \times W_1 \times 100/A\%)^2,$$

wherein $P'^v = \sum_{i=1}^{n} P_i^v; P'\% = \sum_{i=1}^{n} P\%_i = \sum_{i=1}^{n} x_i^P; N'\% = \sum_{i=1}^{n} N\%_i = \sum_{i=1}^{n} x_i^N;$ and $A'\% = \sum_{i=1}^{n} A\%_i = \sum_{i=1}^{n} x_i^A,$ where $x_i$ is the mole fraction of pure component i, P %, N %, A % represent mole percent of paraffin, naphthene, and aromatic content, respectively, in the petroleum fraction, P'%, N'%, A'% represent the paraffin, naphthene, and aromatic contents, respectively, for the petroleum fraction calculated from aggregating pure components in the molecular ensemble using the at least one mixing rule, $P^v$ is the true vapor pressure of the petroleum fraction, and $P'^v$ is the true vapor pressure of the petroleum fraction, calculated from aggregation of pure components in the molecular ensemble.

A set of component concentration data is then generated based upon the optimized comparison data, and the set of component concentration data is displayed to the user.

These and other features of the present invention will become readily apparent upon further review of the following specification and drawings.

BRIEF DESCRIPTION OF THE DRAWINGS

FIGS. 6A and 6B illustrate calculated composition of representative pure components in petroleum naphtha.

FIGS. 7A, 7B, 7C, 7D, 7E and 7F are parity diagrams illustrating property values of naphtha, with the x-axis representing the property values calculated via generalized correlations, and the y-axis representing the property values calculated via the present method for measuring the properties of petroleum fuels by distillation.

FIG. 14A is a parity diagram illustrating the RON of 333 petroleum fractions using the neural network architecture of FIG. 11, with an input parameter of boiling point, with the x-axis representing the RON calculated via generalized correlations, and the y-axis representing the RON calculated via the present method for measuring the properties of petroleum fuels by distillation.

FIG. 14B is a parity diagram illustrating the RON of 333 petroleum fractions using the neural network architecture of FIG. 11, with input parameters of boiling point and RVP, with the x-axis representing the RON calculated via generalized correlations, and the y-axis representing the RON calculated via the present method for measuring the properties of petroleum fuels by distillation.

FIG. 14C is a parity diagram illustrating the RON of 333 petroleum fractions using the neural network architecture of FIG. 11, with input parameters of boiling point and AOS, with the x-axis representing the RON calculated via generalized correlations, and the y-axis representing the RON calculated via the present method for measuring the properties of petroleum fuels by distillation.

FIG. 14D is a parity diagram illustrating the RON of 333 petroleum fractions using the neural network architecture of FIG. 11, with input parameters of boiling point, RVP and AOS, with the x-axis representing the RON calculated via generalized correlations, and the y-axis representing the RON calculated via the present method for measuring the properties of petroleum fuels by distillation.

Similar reference characters denote corresponding features consistently throughout the attached drawings.

DETAILED DESCRIPTION OF THE PREFERRED EMBODIMENTS

The present invention relates to a system and method for predicting physical, performance, perceptual and/or chemical properties of a crude oil or a boiling fraction thereof. As will discussed in detail below, the present analytical method is used to predict a set of data, which consists of global petroleum properties of petroleum products. The overall method utilizes correlative mathematical models.

As will be described in detail below, the present system includes a property estimation apparatus, which estimates the properties of a petroleum product, outputting a property estimate value. The property estimation apparatus utilizes a property estimation model for evaluating the property estimate value. As will be shown below, this property estimate value is compared against a property analyzed value obtained through analyzing the petroleum product, producing a high degree of correlation. The property estimation model may include an optimization algorithm, a neural network algorithm, a regression algorithm, a genetic algorithm, combinations of these or the like.

Figure 1:
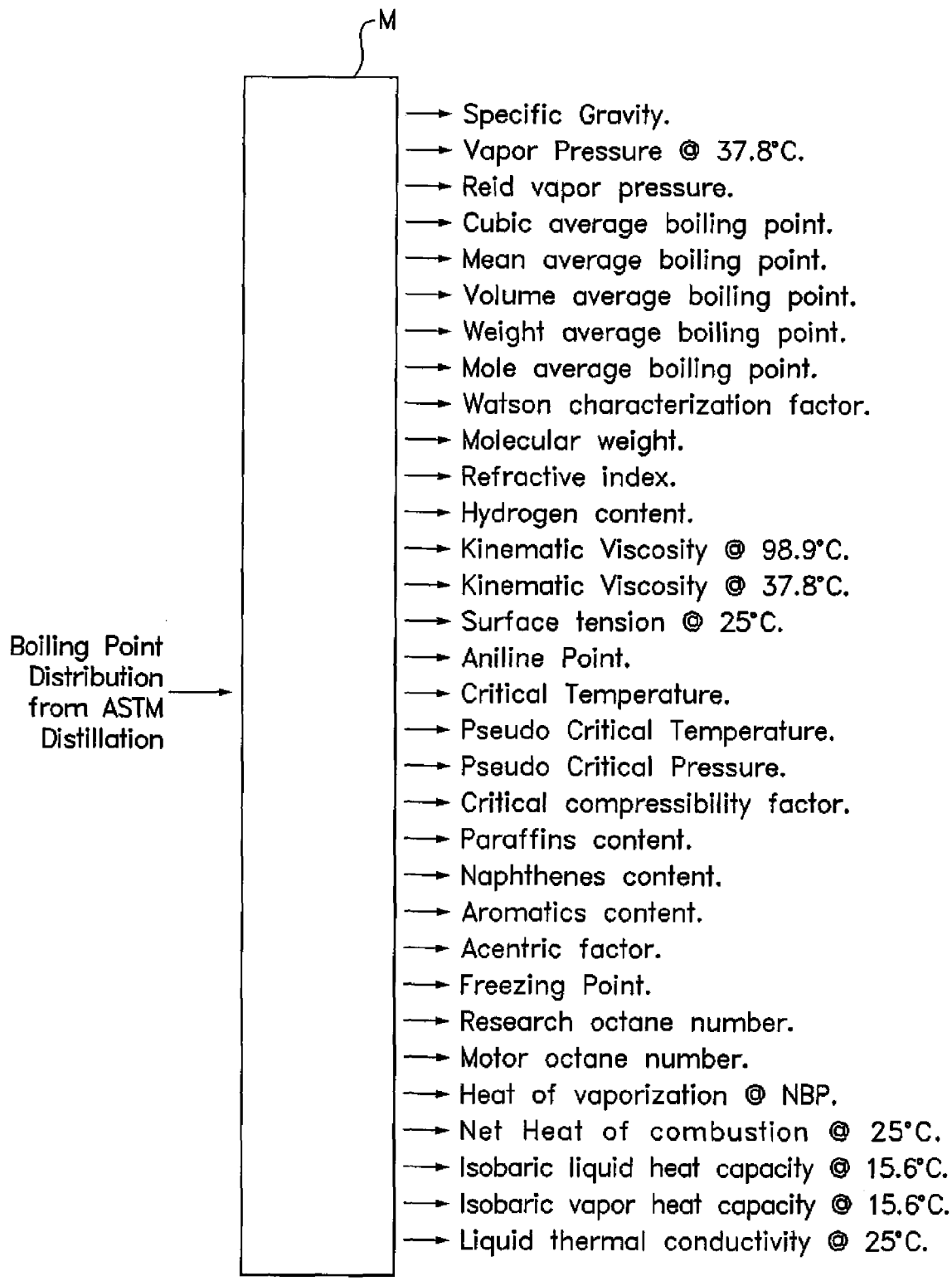
FIG. 1 is a simplified diagrammatic overview of the method for measuring the properties of petroleum fuels by distillation according to the present invention.

The model is used with a conglomeration of distillation data to provide improved recognition of an unknown from its boiling point distribution pattern, as illustrated diagrammatically in FIG. 1 (with the processing model being represented by block M). The particular algorithms of the model allow for the organization and use of assumption-free variables, which already existing in conventional distillation apparatuses, thus producing a comprehensive, discrete and accurate differentiation and matching of thermo-physical and transport properties. Thus, compared with conventional methods, the present method provides increased speeds of fingerprinting analysis, along with increased accuracy and reliability, coupled with decreased time, cost and energy for the analysis.

The method is based on the principle that the molecules forming the various components of a hydrocarbon solution each exhibit physical and chemical characteristics having unique signatures, with these unique signatures being exhibited in terms of boiling point. Further, these physical and chemical characteristics can be correlated either linearly or nonlinearly with regard to volume, mass, or volume percent of the associated component in solution.

Where the properties of the components are known, such as octane, vapor pressure and the like, the volume, mass, or mole percent quantification of these components are used in the present method to characterize the total properties of the hydrocarbon solution. The method includes the vaporization of the hydrocarbon fuel solution in order to determine the boiling points of the various molecular components of the solution. The recorded boiling point data is used to identify the presence of, and to quantify, the volume, mass, or mole percent of the fuel components in solution. From this data, and knowledge of the known properties of the fuel components, the properties of the fuel solution may be calculated.

As will be described below, the method may be used in the prediction of various properties of a $C_5+$ petroleum fraction based on knowledge of the mixture's global properties, which may be easily measured experimentally through, for example, ASTM D86 distillation. The global properties to be measured include boiling point distribution of the various components of the solution. In addition to producing an analysis of the components of a fuel solution, the present method may further be utilized to calculate the properties of light petroleum fractions with high accuracy when at least one bulk property (e.g., ASTM D86 or TBP distillation temperatures) is available.

The method is further utilized to model the complex nature of petroleum fuels by a limited set of representative molecules, thus providing an effective alternative to conventional pseudo-component techniques, and which may further be used with applicability to any petroleum fraction. The method may also be used to represent a broad range of different petroleum feedstocks, with input being based upon a relatively simple set of experiments performed to characterize the attributes of the feed.

The method further provides a molecularly explicit simulation model of feedstock structure and properties that provides a direct input for molecular reaction models, which are ultimately used to map out the changing molecular population with respect to various processing conditions. This method may be utilized to simulate gasoline production processes, including catalytic reforming, alkylation, isomerization, and Fischer-Tropsch gasoline synthesis, as well as the blending of the feeds and products of these processes for gasoline production. Such simulations may be used to increase octane number, improve efficiency, and reduce cost and pollution levels in the processing and production of fuels.

In a preferred embodiment, a known volume of a petroleum sample, which is contained in a vessel, is heated at a regulated rate. The vessel is in communication with a condenser, with preferably 100% of the overall volume being recovered, post-evaporation, by the condenser. When the first evaporated drop appears at the lower end of the condenser tube, a thermometer reading (measuring vapor temperature) is recorded as the initial boiling point (IBP). Temperature readings are recorded at a plurality of volume percentage-of-distillation points, up to the final boiling point (FBP). At the FBP, heating is discontinued and the volume of the remaining liquid is measured and recorded as the recovery product. The boiling point distribution is indicative of the type and amount of the fuel components determined to be characteristic of the fuel component of interest.

Preferably, the boiling point distribution data from the distillation apparatus is processed, with the data being either linearly or nonlinearly correlated to volume percent of the fuel component in solution. The fuel components in solution may be either real components, or may be pseudo-components, with pseudo-components being defined as either boiling point or volume percent cuts.

Alternatively, the boiling point distribution data may be correlated to volume percent of the fuel component in solution using one or more optimization algorithms. As a further alternative, the boiling point distribution data may be correlated to volume percent of the fuel component in solution using simple regression techniques. As a further alternative, the boiling point distribution data may be correlated to volume percent of the fuel component in solution using a neural network.

The boiling point distribution data is used to compute the composition and the properties of the petroleum sample and these properties are then displayed to the user, as will be described in greater detail below. It should be understood that this method may be utilized to calculate and display any suitable set of desired components and properties. Where a plurality of components are of interest, a plurality of distillation apparatuses and associated boiling point distribution detectors may be utilized, with the plurality of detection data sets being processed and then combined in an additive process to obtain total properties for the fuel.

In a first example, a molecularly explicit property prediction (MEPP) model is developed according to the present method, with the MEPP being tested using a molecular ensemble consisting of 68 molecules to characterize and predict the properties for thirty different petroleum naphtha samples. The results are found to be in excellent agreement with conventional prediction methods based on global properties.

Figure 2:
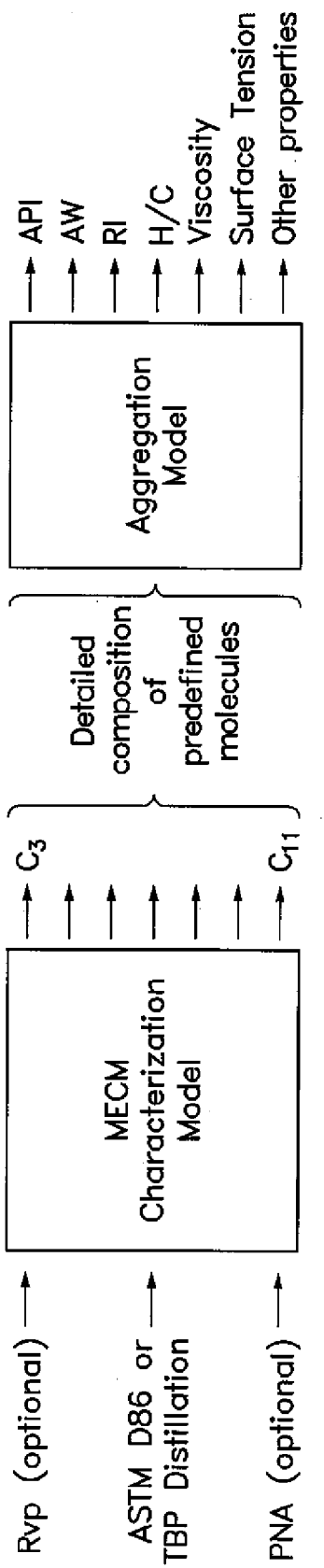
FIG. 2 is diagrammatic overview of the method for measuring the properties of petroleum fuels by distillation according to the present invention.

In this embodiment, a property prediction model is based on the principle that the global properties of a petroleum fraction, such as the true boiling point (TBP) distribution, vapor pressure, or PNA fractional composition, for example, must be equal to those calculated from the pure components forming that petroleum fraction. When some bulk and pure component properties are available, the composition of a limited set of pure components in the petroleum fraction may be predicted using one or more optimization algorithms, as diagrammatically illustrated in FIG. 2. The predicted composition may then be used to predict the other global properties of the petroleum fuel using appropriate mixing rules.

The standard input global-properties for the model are the petroleum fraction distillation data, which may be the ASTM D86 standard test method for distillation of petroleum products at atmospheric pressure, the TBP, SimDist simulated distillation analysis or the like, along with the Reid vapor pressure (RVP), and the PNA content. The internally calculated global properties are the molecular weight, the true vapor pressure at 37.8° C., the specific (API) gravity, the cubic average boiling point (CABP), the mean average boiling point (MeABP), the volumetric average boiling point (VABP), the weight average boiling point (WABP), the molar average boiling point (MABP), the Watson characterization factor ($K_w$), the refractive index, the carbon-to-hydrogen content, the kinematic viscosity at 37.8 and 98.9° C., the surface tension of liquid at 25° C., the aniline point, the cloud point, the true and pseudo-critical temperatures and pressures, the critical compressibility factor, the acentric factor, the flash point, the freezing point, the heat of vaporization at the normal boiling point, the net heat of combustion at 25° C., the isobaric liquid and vapor heat capacities at 15.6° C., the liquid thermal conductivity at 25° C., and the research and motor octane numbers. The internally calculated global properties of the petroleum fraction may be determined using any suitable conventional methods.

The above analytical input (distillation data, RVP, and PNA content) and the computationally predicted internal properties are also calculated from pure components data. The two methods are contrasted and the difference is minimized using an optimization algorithm. The model output is a computationally generated explicit atomic detail of the petroleum feedstock. This outcome molecular ensemble retains the qualitative features that mimic light petroleum fractions in terms of thermodynamic and transport properties.

Experimental values of the RVP and PNA content are preferable. However, if not supplied as input, they are calculated using the ASTM D86 distillation or the true boiling point (TBP) as the only experimental data required as input. The availability of other input properties, such as, for example, the API gravity is an additional benefit to improve the model predictions, but is not essential to the method.

In the following, the conventional Molecularly Explicit Characterization Model (MECM) is used in the simulation of light petroleum fractions, with the MECM model being used to determine the optimum molecular distribution in petroleum fractions. The concentration of a pre-selected set of representative true-components is calculated using the global, as well as the internal and structural, properties of the petroleum fraction.

It is found that it not essential for all the properties of the petroleum fuel to be optimized against those from the pure components. In fact, only the ASTM D86 distillation, the PNA content and the RVP are necessary to provide a feasible solution. All of the other properties calculated from the bulk properties of the petroleum fraction, and those from the pure components within, were almost identical. Thus, it is concluded that the properties of a petroleum fraction can be estimated from the above three properties alone (i.e., ASTM D86 distillation, the PNA content and the RVP).

Since generalized correlations are widely available for PNA fractional composition and RVP, complete characterization can be obtained from the knowledge of only the ASTM D86 distillation data. The MECM model is enhanced with property prediction capabilities to provide a new molecularly explicit property prediction (MEPP) model that can be used to predict the properties of light petroleum fractions using ASTM D86 distillation data alone.

With regard to the MEPP model, the average (i.e., global) physical property of the petroleum fraction $\Theta$ can be calculated by integration of the pure component properties along the true boiling point curve according to the following relation:

$$\Theta = \int_0^1 \Theta(x) dx \quad (1)$$

where x is the fraction of volume vaporized in a TBP distillation, and $\Theta(x)$ is the property value at x.

For a finite number of increments (i.e., components), the solution of the integral term in equation (1) may be attained by calculating the area under the property distribution curve, and equation (1) may be approximated by the following expression representing that area:

$$\Theta = \Sigma_{i=1}^n \Theta_i(x) \Delta x_i \quad (2)$$

where n is the number of increments (i.e., pure components in the molecular ensemble), $\Delta x$ is the increment size (i.e., the volume fraction of the pure components), and $\Theta_i(x)$ is the property value or a function thereof for the increment $\Delta x_i$ (or, the pure component).

Since some pure component properties do not mix linearly, mixing rules may be applied to estimate the properties of the defined mixture. Thus, the above relation may be used to predict the composition of the pure components x from the knowledge of the physical properties of these components and those of the mixture.

Figure 3:
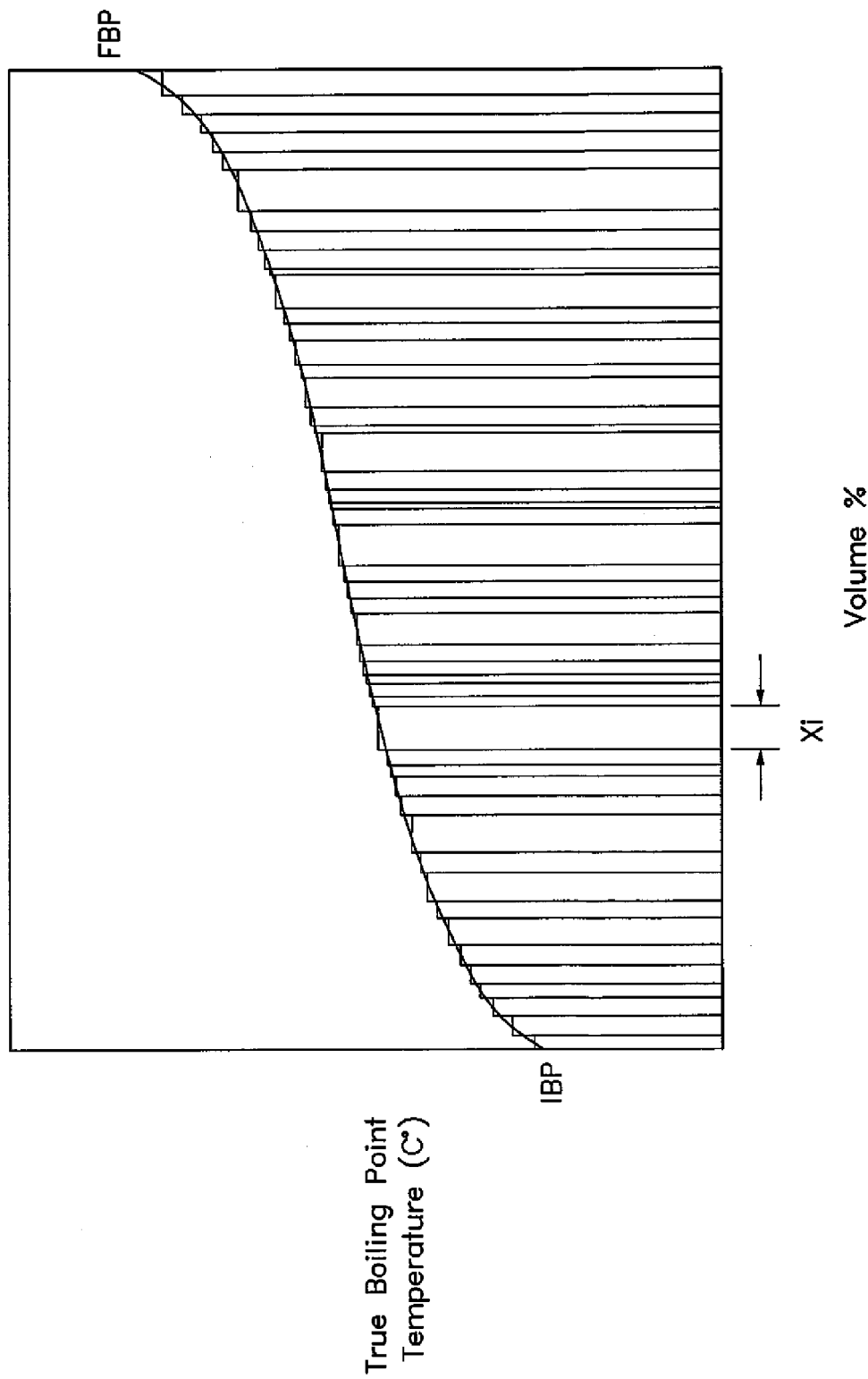
FIG. 3 is a graph illustrating a simulation of a true boiling point curve produced by the present method for measuring the properties of petroleum fuels by distillation.

In the MECM model, a petroleum fraction is divided into a number of increments along the true boiling point (TBP) curve, as illustrated in the sample graph of FIG. 3. This is equal to the number of pre-selected representative true compounds for which the concentration is to be determined. Since the number of components used in the model is finite, the above equation does not need to be integrated and, instead, mixing rules may be applied. For example, in order to relate the API of a petroleum cut to that of the pure components in it, the specific gravity (SG) at 15.6° C. is used (since API does not mix linearly) and the above property relation may be re-written as:

$$SG = \int_0^1 SG(x) dx. \quad (3)$$

For a finite number of components n, this relation may be reduced to the following form:

$$SG = \Sigma_{i=1}^n (SG)_i (x_w)_i \quad (4)$$

where $(x_w)_i$ is the mass fraction of the true-component i in the petroleum cut. Similar relations may be produced for other properties, which may be solved for x (i.e., the pure component concentrations) using an optimization algorithm.

The theoretical background of the MECM model is presented in Albahri, T., 2005, "Molecularly Explicit Characterization Model (MECM) for Light Petroleum Fractions", *Ind. Eng. Chem. Res.* 44, 9286-9298, which is herein incorporated by reference in its entirety. The MECM was improved further by incorporating it into the MEPP model to make it viable for property prediction purposes, as shown in Albahri, T., "Enhanced Method for Predicting the Properties of Petroleum Fractions", *Prepr. Pap.-Am. Chem. Soc., Div. Fuel Chem.* 2004, 49(2), 925. The logic diagram for this method is depicted in FIG. 4, which illustrates the methodology used to develop the MEPP model and the procedure followed to analyze the simulation problem.

Figure 4:
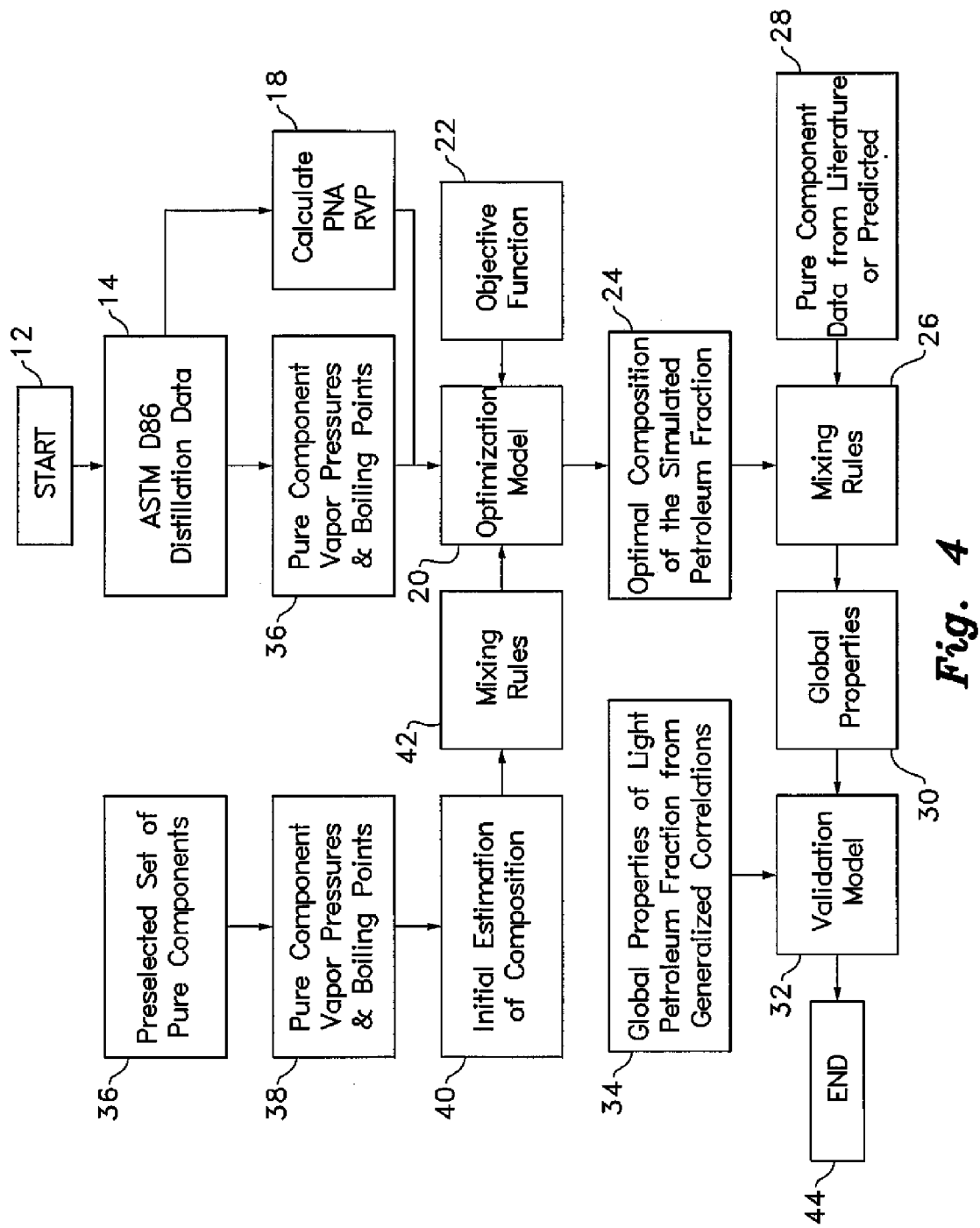
FIG. 4 is a block diagram illustrating the method for measuring the properties of petroleum fuels by distillation according to the present invention.

As shown in FIG. 4, the process begins at 12, with information being gathering about a particular light petroleum fraction (for example, naphtha) from existing plants or available literature. In order to characterize the unknown hydrocarbon mixture, laboratory analysis is used to determine the API gravity, the RVP, the PNA content and TBP. These experimental procedures provide the input to the molecular feedstock simulation. Out of these four properties, only the TBP must be available (as is usually the case), while the other properties, if not available, may be estimated. The other global properties of the petroleum fraction are calculated internally by the MECM model. The TBP is provided by ASTM D86 distillation data at step 14, with the pure component vapor pressures and boiling points being extracted from this data at step 36. The PNA and RVP, if not available, are calculated via the MECM model at step 18.

Next, a molecular ensemble including 68 molecular species is used as an example to simulate petroleum naphtha, as shown in Table 2:

TABLE 2

Molecular ensemble used to characterize petroleum naphtha

| | |
|---|---|
| 1 | Propane |
| 2 | isobutane |
| 3 | n-butane |
| 4 | 2-methyl butane (isopentane) |
| 5 | n-pentane |

TABLE 2-continued

Molecular ensemble used to characterize petroleum naphtha

| | |
|---|---|
| 6 | Cyclopentane |
| 7 | 2,2-dimethyl butane (neohexane) |
| 8 | 2,3-dimethyl butane |
| 9 | 2-methyl pentane |
| 10 | 3-methyl pentane |
| 11 | N-hexane |
| 12 | methylcyclopentane |
| 13 | 2,2-dimethylpentane |
| 14 | Benzene |
| 15 | 2,4-dimethylpentane |
| 16 | Cyclohexane |
| 17 | 2,2,3-trimethylbutane (Triptane) |
| 18 | 3,3-dimethylpentane |
| 19 | 1,1-dimethyl cyclopentane |
| 20 | 2,3-dimethylpentane |
| 21 | 2-methylhexane |
| 22 | cis-1,3-dimethylcyclopentane |
| 23 | 1,2-dimethyl cyclopentane-trans |
| 24 | 3-methylhexane |
| 25 | trans-1,3-dimethylcyclopentane |
| 26 | 3-ethylpentane |
| 27 | N-heptane |
| 28 | Ethylcyclopentane |
| 29 | 2,2-dimethylhexane |
| 30 | 2,5-dimethylhexane |
| 31 | 2,4-dimethylhexane |
| 32 | 2,2,3-trimethylpentane |
| 33 | Toluene |
| 34 | 3,3-dimethylhexane |
| 35 | 2,3-dimethylhexane |
| 36 | 2-methyl-3-ethylpentane |
| 37 | 2-methylheptane |
| 38 | 3,4-dimethylhexane |
| 39 | 4-methylheptane |
| 40 | 3-methyl-3-ethylpentane |
| 41 | 3-ethylhexane |
| 42 | 3-methylheptane |
| 43 | cis-1,3-ethylmethylcyclopentane |
| 44 | trans-1,2-ethylmethylcyclopentane |
| 45 | trans-1,3-ethylmethylcyclopentane |
| 46 | 2,2,5-trimethylhexane |
| 47 | N-octane |
| 48 | cis-1,2-ethylmethylcyclopentane |
| 49 | 2,3,5-trimethylhexane |
| 50 | 2,2-dimethylheptane |
| 51 | 2,4-dimethylheptane |
| 52 | 2-methyl-4-ethylhexane |
| 53 | 2,6-dimethylheptane |
| 54 | 2,5-dimethylheptane |
| 55 | 3,5-dimethylheptane |
| 56 | Ethylbenzene |
| 57 | 3,3-dimethylheptane |
| 58 | P-xylene |
| 59 | M-xylene |
| 60 | 2,3-dimethylheptane |
| 61 | 3,4-dimethylheptane |
| 62 | 4-ethylheptane |
| 63 | 4-methyloctane |
| 64 | 3-ethylheptane |
| 65 | 2-methyloctane |
| 66 | o-xylene |
| 67 | 3-methyloctane |
| 68 | n-nonane |

The pure component properties are then collected from available literature and the like. In the absence of a certain property value for a molecule, common correlations for various physical properties, which are widely available, may be used to estimate it.

This method is used to provide a unique identity to each of the ensemble molecules. The identification of each unique component is crucial not only to the description of complex feedstocks, but for the development of molecular reaction models and the prediction of product properties.

An important challenge in modeling refinery processes is the development of a reliable yet practical molecularly explicit characterization model for complex feedstocks, where the number of components is not too excessive for computational power (during kinetic modeling and rigorous phase equilibrium calculations) or too diminutive for modeling purposes.

The catalytic cracking of n-heptane alone, for example, is reported to undergo 2,210 reactions and 336 intermediates. When the feed is a complex mixture, such as naphtha or gas oil containing thousands of hydrocarbons, the number of components in the reaction mixture becomes enormous and the generation of reaction networks for each of the feed components becomes an overwhelming task. For that reason, predicting molecular compositions of $10^4$ molecules in petroleum and its fractions is impractical for use in kinetic modeling. It also does not account for all the inherent molecular species, from which 1,500 have been so far identified in gasoline alone. Molecule-by-molecule separation and identification is presently impossible, via conventional methods, for naphtha, not to mention resides, asphaltenes and even very heavy oils.

For this reason, the present model does not account for the 10,000 or more components of petroleum fractions, as that is impractical for modeling needs. Rather, the model accounts for a limited set of pure components that are capable of representing the whole petroleum fraction. The set chosen here (using the example of simulating naphtha) includes 68 model-compounds chosen in such a way as to account for the overall components that exist in the fraction. This reduces the number of parameters and results in large computational savings.

The final number of model components is arrived at by screening over 200 pure components based on background knowledge of structural chemistry and relative volatility, in addition to other criteria available in the literature. It should be noted that special emphasis is placed on the important role the structure of the molecule plays in catalytic chemistry in petroleum refining processes.

In FIG. 4, the preselected set of pure components are input at step 36, along with the corresponding pure component vapor pressures and boiling points. The initial estimation of composition, noted above, occurs at step 42. Model compounds of the selected molecular ensemble are further based on conditional arguments calculated from initial boiling point considerations and basic structural logic. Selection of the components is performed by considering, first, that each petroleum fraction can be represented by a finite number of true-components having boiling points within the boiling range of the petroleum cut. Naphtha feedstocks, for example, are typically the 20-200° C. distillates of the crude oil. These fractions are operationally defined, and therefore their exact boiling range is dependent upon the actual separation conditions. Consideration is also made to the molecular product fraction (i.e., paraffin, naphthene and aromatic content).

Further general guidelines used for the selection of the molecular ensemble to represent the petroleum fraction relate to the boiling point. Straight-run naphtha for example, which is the typical feedstock for gasoline production, consists of material boiling between pentane and kerosene distillate, including primarily paraffinic, naphthenic, and aromatic hydrocarbons with 3 to 11 carbon atoms per molecule. This corresponds, approximately, to a boiling range of 20 to 200° C. at 1 atm. Thus, the model compounds must be composed of normal and isoparaffins, naphthenes, and aromatics ranging in carbon number from $C_3$ through $C_{11}$. This must include such compounds as benzene, cyclopentane, cyclohexane and homologous series of these. Additionally, if more than one isomer for a compound exists in the fraction, then only one or two that best represent the physical and chemical properties of all the isomers is selected. Another criterion relates to the order of carbenium and carbonium ions that are likely to form during the kinetic modeling of catalytic cracking mechanism on bi-functional zeolite catalysts, which is important in kinetic research. Having satisfied the above criteria, the final molecular ensemble consisting of 68 molecular species, shown in Table 2, were used to simulate petroleum naphtha.

The next step in the method includes the use of mixing rules to calculate, from the predefined pure component data (molecular description, boiling points and composition), the concentration of the light components (at step 42) using the input RVP, then the composition of the heavier components using the PNA fractional composition and the boiling point distribution.

Following application of the mixing rules at step 42, the input vapor pressures and boiling points, along with the calculated PNA and RVP values, are optimized (at step 20), using any suitable type of optimization algorithm, along with any suitable necessary objective functions (step 22) to produce the optimal composition of the simulated petroleum fraction (at step 24).

As noted above, the pure component data, which may be provided from readily available external sources, such as the available literature, or through prediction, is input (step 28) with mixing rules being applied at 26 to both this data, as well as the calculated optimized composition of the simulated petroleum fraction. Global properties can then be extracted at 30. The predicted global properties of the simulation, produced at step 30, may be compared through any suitable type of validation or comparison model (at step 32) against known global properties of light petroleum fractions from generalized correlations (step 34), with the process ending at 44. These latter steps, including the simulation outcome in terms of molecular (boiling point) distributions and PNA fractional composition, are used to compare and contrast the experimental and analytical procedures.

When molecular detail is available, it is possible to predict analytical results for multi-component mixtures through simple accounting or methods for aggregating the molecules into lumped fractions. The properties shown below in Table 3 are calculated from global properties and the aggregation of pure components, which must match, otherwise model consistency and internal integrity is lost:

TABLE 3

Comparison of global properties of light reformate calculated from generalized correlations and from aggregation of pure components using MEPP model

| Property | Experimental or predicted from experimental | MECM simulation | % Error (deviation) |
|---|---|---|---|
| Specific Gravity | 0.7143 | 0.7083 | −0.84 |
| Vapor Pressure @ 37.8° C., bar. | 0.7033 | 0.7033 | 0 |
| Reid vapor pressure, bar | 0.655 | 0.655 | 0 |
| Cubic average boiling point, ° C. | 87.7 | 82.6 | −1.44 |
| Mean average boiling point, ° C. | 84.4 | 81.1 | −0.94 |
| Volume average boiling point, ° C. | 89.3 | 84.1 | −1.45 |
| Weight average boiling point, ° C. | 90.3 | 87.1 | −0.92 |
| Mole average boiling point, ° C. | 81.6 | 79.6 | −0.57 |
| Watson characterization factor | 12.09 | 12.18 | 0.77 |
| Molecular weight, gm/mole | 93.5 | 93.1 | −0.42 |
| Refractive index | 1.3973 | 1.396 | −0.09 |
| Hydrogen content, wt frac. | 0.1458 | 0.1507 | 3.34 |
| Kinematic Viscosity @ 98.9° C., mm²/sec | 0.32 | 0.31 | −3.56 |
| Kinematic Viscosity @ 37.8° C. mm²/sec | 0.48 | 0.49 | 1.7 |
| Surface tension @ 25° C. dynes/cm | 20.44 | 19.48 | −4.7 |
| Aniline Point, ° C. | 37.8 | 57.1 | 6.21 |
| Critical Temperature, ° C. | 265.6 | 261.3 | −1.51 |
| Pseudo Critical Temperature, ° C. | 254.4 | 254.8 | 0.14 |
| Pseudo Critical Pressure, psia | 31.03 | 31.23 | 0.67 |
| Critical compressibility factor | 0.2773 | 0.2664 | −3.91 |
| Paraffins content, mole % | 71.5 | 70.88 | −0.87 |
| Naphthenes content, mole % | 17.19 | 17.43 | 1.43 |
| Aromatics content, mole % | 11.3 | 11.7 | 3.34 |
| Acentric factor | 0.284 | 0.285 | 0.32 |
| Freezing Point, ° C. | −102.3 | −104.7 | −1.44 |
| Research octane number | 72.3 | 73.2 | 1.23 |
| Motor octane number | 70 | 71.7 | 2.37 |
| Heat of vaporization @ NBP, J(abs)/gm | 322.08 | 323.06 | 0.31 |
| Net Heat of combustion @ 25° C. J(abs)/gm | 44,245 | 44,047 | −0.11 |
| Isobaric liquid heat capacity @ 15.6° C., J(abs)/gm K | 2.437 | 2.039 | −16.38 |
| Isobaric vapor heat capacity @ 15.6° C., J(abs)/gm K | 1.882 | 1.604 | −14.79 |
| Liquid thermal conductivity @ 25° C., J(abs)/sec-m²-K/m | 0.1099 | 0.1161 | −9.08 |

In the above, the MECM simulation comes from aggregation of pure components, and the heat of vaporization NBP is at 0 psig and MeABP.

Molecular structure properties are computed by simply counting their occurrence with respect to composition. The averaged properties $\Theta$ are computed using weight, mole, or volume fractions as appropriate, where $f(\Theta)_i$ may be the property of pure component i or a function thereof:

$$\Theta = \Sigma_{i=1}^{n}(\Theta_i)x_i. \quad (5)$$

It should be understood that methods and equations for aggregating the properties of molecules using mixing rules for calculating global properties of mixtures are known, and any such methods may be utilized. For the surface tension, average molecular weight, pseudo-critical temperature, critical compressibility factor, acentric factor, vapor pressure, refractive index, aniline point, freezing point and octane number, a simple mole average method is used. A mass fraction average method is used for the heat of vaporization, the net heat of combustion, the isobaric heat capacity for vapor and liquid and Watson's characterization factor, while volume fraction is used for the specific gravity.

For example, the molecular weight of the petroleum fraction can be calculated from the molecular weight of the pure components and their mole fractions using the following mixing rule:

$$MW = \sum_{i=1}^{n} (MW)_i (x)_i. \tag{6}$$

The average boiling points are calculated using the API-recommended methods, as follows:

$$VABP = \sum_{i=1}^{n} x_{vi} T_{bi} \tag{7}$$

$$MABP = \sum_{i=1}^{n} x_i T_{bi} \tag{8}$$

$$WABP = \sum_{i=1}^{n} x_{wi} T_{bi} \tag{9}$$

$$CABP = \left(\sum_{i=1}^{n} x_{vi} T_{bi}^{1/3}\right)^3 \tag{10}$$

$$MeABP = \frac{MABP + CABP}{2} \tag{11}$$

where VABP is the volumetric average boiling point, MABP is the molal average boiling point, WABP is the weight average boiling point, CABP is the cubic average boiling point, MeABP is the mean average boiling point, $T_{bi}$ is the normal boiling point of component i (in K or °R), $x_{vi}$ is the volume fraction of component i, $x_i$ is the mole fraction of component i, and $x_{wi}$ is the weight fraction of component i.

The Watson characterization factor is calculated using the weight average as:

$$K_w = \sum_{i=1}^{n} x_{wi} K_{wi}. \tag{12}$$

The paraffin, naphthene and aromatics content is calculated by adding the mole, weight or the volume fraction of the compounds belonging to each group as follows:

$$\Omega = \sum_{i=1}^{n_\Omega} x_{i(\Omega)} \tag{13}$$

where $\Omega$ is paraffin, naphthene, or aromatics content in either the weight, mole, or volume fraction, whereas $x_i$ is the weight, mole, or volume fraction, respectively.

The hydrogen content in mole fraction is calculated by adding the fractional amount of hydrogen atoms from all the molecules as follows:

$$H_2 = \sum_{i=1}^{n} x_i (n_{H_2})_i \tag{14}$$

where $x_i$ is mole fraction of molecular component i in the defined mixture and $(n_{H_2})_i$ is the number of hydrogen atoms in molecule i.

For the critical temperature, critical and pseudo-critical pressures, kinematic viscosity, and thermal conductivity, simple linear mole, weight or volume averages are not appropriate and more intricate mixing rules must be used. The true critical temperature for the defined mixture is calculated from that of the pure components using a nonlinear averaging of the true critical temperature using the surface fraction as:

$$Tc_m = \sum_{i=1}^{n} Tc_i \Phi_i \tag{15}$$

where $\phi_i$ is the surface fraction calculated as:

$$\Phi = \frac{x_i Vc_i}{\sum_{j=1}^{n} x_j Vc_j} \tag{16}$$

and, $x_i$ is the mole fraction of component i, $Vc_i$ is the critical volume of component i, $Tc_i$ is the critical temperature of component i, and $Tc_m$ is the true critical temperature of the mixture.

For the pseudo-critical pressure, a simple mole fraction average of the pure component critical pressure is normally not satisfactory. The simplest rules that gives acceptable results are the following combination:

$$Pc_m = \frac{RTc_m \left(\sum_{i=1}^{n} Zc_i y_i\right)}{\sum_{i=1}^{n} Vc_i y_i} \tag{17}$$

where $Tc_m$ is the pseudo-critical temperature of the mixture, $Vc_i$ is the critical volume of component i, $Zc_i$ is the critical compressibility factor of component i, $y_i$ is the mole fraction of component i, and R is the ideal gas constant.

The true critical pressure for the defined mixture is calculated using the method of Chueh and Prausnitz by the modified Redlich-Kwong equation of state as:

$$Pc_T = \frac{RTc_T}{Vc_T - b_m} - \frac{a_m}{Tc_T^{1/2} Vc_T (Vc_T + b_m)} \tag{18}$$

where $Tc_T$ is the true critical temperature of the mixture, $Vc_T$ is the true critical volume of the mixture, R is the ideal gas constant, and $a_m$ and $b_m$ are constants to be determined from mixing rules and interaction parameters.

The kinematic viscosity for the defined mixture at the standard temperatures of 37.8 and 98.9° C. is calculated from that of the pure components, using nonlinear mole fraction averaging as follows:

$$\ln v_m = \sum_{i=1}^{n} x_i \ln v_i. \tag{19}$$

For the liquid thermal conductivity, simple mole and mass fraction averaging is found to be equally effective in the following expression:

$$\frac{1}{K_m} = \sum_{i=1}^{n} \frac{x_i}{K_i}. \quad (20)$$

Step 20 in FIG. 4 utilizes an optimization algorithm that calculates the optimum molecular composition of the simulated petroleum fraction. The objective function (step 22) compares the true boiling point distribution of the petroleum fraction (from step 14) with those of the molecular representation (from step 36) while incorporating additional constraints from structural relations within the petroleum fraction, such as the PNA fractional composition and other relations, such as the vapor pressure, to improve the simulation output and provide the model with a general validity. For that purpose, it is essential to allow for not only the initial transformation of feedstock characterization information into a molecular representation, but also the inverse transformation of molecular representation into global properties.

The distribution of the molecular ensemble in the MEPP model is determined in terms of volume fractions by minimizing the following objective function modified from that of the MECM model:

$$S = \sum_{j=1}^{n} ((Tb_j - T'b_j) \times W_o \times 100/Tb_j)^2 + \quad (21)$$

$$((PNA - PNA') \times W_1 \times 100/PNA)^2$$

where j is the index number of the molecule and n is the total number of molecules. PNA is the paraffin, naphthene, and aromatic content for the petroleum fraction determined either experimentally or calculated from experiment using generalized correlations with the bulk (global) properties as input parameters. PNA' is the paraffin, naphthene, and aromatic content for the petroleum fraction calculated from aggregating pure components in the molecular ensemble using mixing rules. T'b$_j$ is the boiling point of pure component j and Tb$_j$ is the boiling point value on petroleum fractions TBP curve corresponding to component j. W$_0$ is the weighting factor for the boiling points and W$_1$ is the weighting factor for the PNA fractional composition. S is the objective function to be minimized.

The objective function is taken as the sum of the square of the % error between the observed (experimental or otherwise predicted from experimental) TBP and PNA content of the petroleum fraction and those calculated from mixing (aggregating) the components of the molecular ensemble. The objective function consists of two parts: The first part compares the boiling point of the pure component to the boiling point on the TBP curve of the petroleum fraction corresponding to the concentration (or cumulative volume %) of that component. By minimizing the objective function, the difference between the boiling points is reduced by manipulating the composition of the molecular ensemble in the simulated mixture until each molecules boiling point matches that on the TBP curve.

The second part of the objective function compares the PNA fractional composition of the petroleum fraction and those from aggregation of the molecular ensemble. By minimizing the objective function the difference in these properties for the petroleum fraction and the molecular ensemble is reduced while the composition of the pure components in the molecular ensemble mixture simulating the petroleum fraction is calculated. As such, the petroleum fraction is characterized using a molecular ensemble with average physical properties (e.g., specific gravity, molecular weight, etc.) close to that of the petroleum fraction.

The above objective function may be expanded to all the parameters involved as follows (equation (22)):

$$S = \sum_{j=1}^{n} ((Tb_j - T'b_j) \times W_o \times 100/Tb_j)^2 +$$

$$((P\% - P\%') \times W_1 \times 100/P\%)^2 +$$

$$((N\% - N\%') \times W_1 \times 100/N\%)^2 +$$

$$((A\% - A'\%) \times W_1 \times 100/A\%)^2$$

where $P'^v = \sum_{i=1}^{n} P_i^v$; $P'\% = \sum_{i=1}^{n} P\%_i = \sum_{i=1}^{n} x_i^P$;

$N'\% = \sum_{i=1}^{n} N\%_i = \sum_{i=1}^{n} x_i^N$; and $A'\% = \sum_{i=1}^{n} A\%_i = \sum_{i=1}^{n} x_i^A$, where P %, N %, A % are the mole percent of paraffin, naphthene, and aromatic content, respectively, in the petroleum fraction determined experimentally or calculated from experiment using generalized correlations with the global properties as input parameters, while P'%, N'%, A'% are the paraffin, naphthene, and aromatic contents, respectively, for the petroleum fraction calculated from aggregating pure components in the molecular ensemble using mixing rules. P$^v$ is the true vapor pressure of the petroleum sample determined experimentally or predicted from experiment, and P'$^v$ is the same, calculated from aggregation of pure components in the molecular ensemble. In the above, the following constraints are used: $\Sigma x_i = 1$ and $\forall x_i \geq 0$.

In the above objective function, both PNA' and Tb$_j$ are functions of composition. The first utilizes the molecular composition in mixing rules, while the second is a polynomial fit of the TBP curve of the petroleum fraction, in which the composition is expressed in volume percent as follows:

$$T'_{bj} = T_0 + a\Psi_j + b\Psi_j^2 + c\Psi_j^3 + d\Psi_j^4 \quad (23)$$

where a, b, c, and d are constants estimated by regression from the TBP curve of the petroleum fuel.

Alternatively, the probability density function may be used in the following form:

$$\frac{T_j - T_0}{T_0} = \left[\frac{T_1}{T_2} \ln\left(\frac{1}{1-\Psi_j}\right)\right]^{1/T_3} \quad (24)$$

where T$_0$, T$_1$, T$_2$ and T$_3$ are constants that can be estimated by regression using the TBP curve of the petroleum fraction.

In the above equations, $\Psi_j$ is the cumulative volume fraction at the mid-volume percent of component j given by the following equation with x$_v$ as the volume fraction:

$$\Psi_j = \sum_{k=1}^{j-1} x_{vk} + \frac{x_{vj}}{2}. \tag{25}$$

Figure 16:
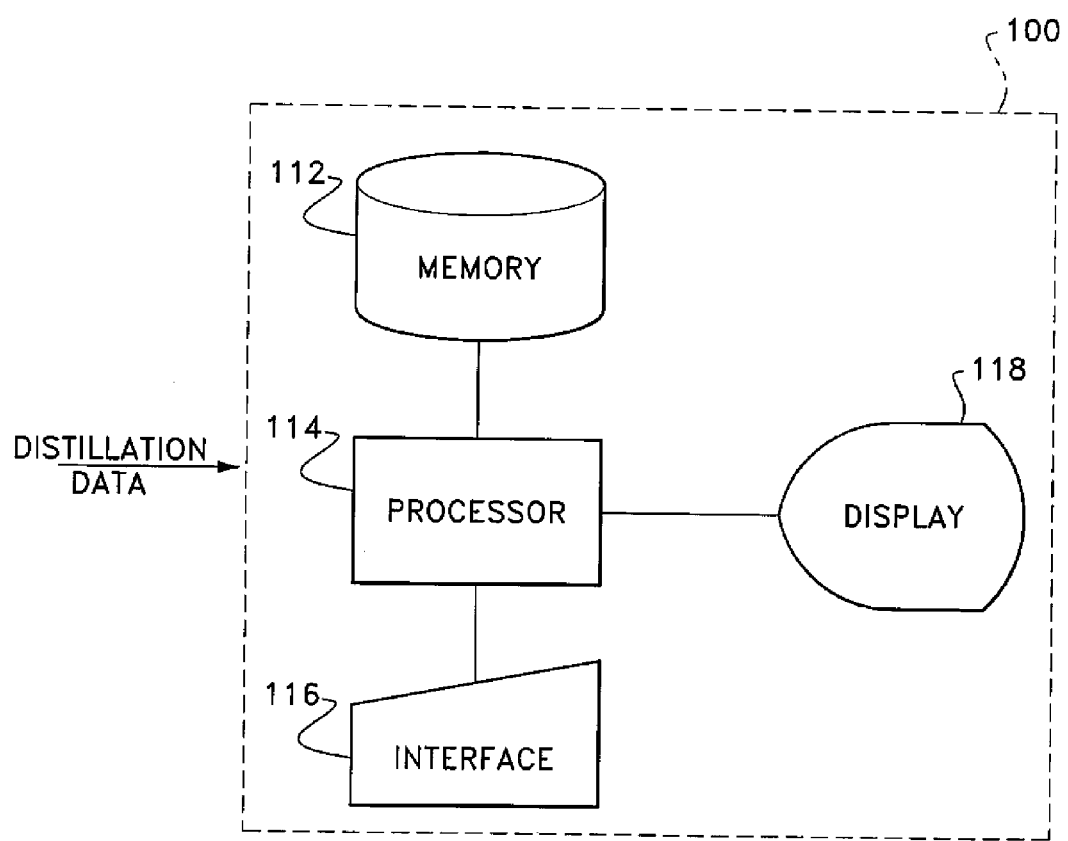
FIG. 16 diagrammatically illustrates a system for measuring the properties of petroleum fuels by distillation according to the present invention.

FIG. 16 illustrates a system 10 for performing the above calculations. system 10 includes a controller 100 for receiving the initial distillation data (from steps 14 and 36 in FIG. 4). It should be understood that the calculations may be performed by any suitable computer system, such as that diagrammatically shown in FIG. 16. Data is entered into controller 100 of system 10 via any suitable type of user interface 116, and may be stored in memory 112, which may be any suitable type of computer readable and programmable memory. Calculations are performed by processor 114, which may be any suitable type of computer processor and may be displayed to the user on display 118, which may be any suitable type of computer display. Preferably, processor 114 is associated with, or includes, at least one neural network.

Processor 114 may be associated with, or incorporated into, any suitable type of computing device, for example, a personal computer or a programmable logic controller. The display 118, the processor 114, the memory 112 and any associated computer readable recording media are in communication with one another by any suitable type of data bus, as is well known in the art.

Examples of computer-readable recording media include a magnetic recording apparatus, an optical disk, a magneto-optical disk, and/or a semiconductor memory (for example, RAM, ROM, etc.). Examples of magnetic recording apparatus that may be used in addition to memory 112, or in place of memory 112, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

In a further example, a pseudo-component property prediction model is similarly developed to measure the density of petroleum fractions using 100, 5, and 1 pseudo-component cuts, respectively, and this too is found is found to be in excellent agreement with experimental data. As will be described in greater detail below, artificial neural networks were further used to predict the specific gravity (SG), Reid vapor pressure (RVP), and research octane number (RON), and were also found to be in excellent agreement with experimental data.

The mathematical fitting of the TBP curve in equations (23) and (24) is a source of an unlimited number of boiling point values to be compared with those of an unlimited number of molecules. Thus, there will always be an equal number of variables, both independent (boiling points) and dependent (concentrations), using only the true boiling point distribution, regardless of the number of molecules chosen. Therefore, no matter how many molecules are used in the ensemble, it is always possible to find a feasible solution.

The sum of the squares of the percentage errors of the boiling points in the first line of the objective function [equations (21) and (22)] is much greater than that of the PNA content in the second line because the number of molecules in the ensemble n is 68. For that reason, a weighting factor is used in each part of the objective function to give equal account of the other properties, which would, otherwise, be overwhelmed by the errors from the boiling points of such a large number of molecules. The optimum weighting factors $W_1:W_0$ chosen to be approximately 25:1 produces a very good reproduction of the TBP curve, as well as the other global properties of the naphtha (e.g., the API gravity, molecular weight, PNA content, etc.). In the event that the number of molecules in the ensemble is reduced, $W_1$ must also be reduced to accommodate the changes and produce the minimum error possible. Once the optimum values of the weighting factors are determined, they are kept constant throughout the method, since they are a function of the number of both molecules and properties considered.

The molecular group-type (paraffins, naphthenes and aromatics) fractional composition for the naphtha can be obtained experimentally using gas chromatography or similar techniques. Alternatively, when experimental data is not available, these structural relations may be predicted, from the conventional properties, using conventional methods. For example, the API-TDB EPCON software-based method may be used to obtain an estimation of the PNA fractional composition of feed fractions. The API-TDB EPCON method estimates the mole fractions of the paraffins XP, naphthenes XN and aromatics XA, using the following equations:

$$X_P = -23.94 + 24.21R_i - 1.092\text{VGF} \tag{26}$$

$$X_N = 41.14 - 39.43R_i + 0.672\text{VGF} \tag{27}$$

$$X_A = -16.2 + 15.22R_i + 0.465\text{VGF} \tag{28}$$

$$R_i = n - (d/2) \tag{29}$$

$$\text{RI} = [(1+2i)/(1-i)]^{1/2} \tag{30}$$

$$\text{VGF} = -1.816 + 3.484\text{SG} - 0.1156\upsilon_{38} \tag{31}$$

where $R_i$ is the refractivity intercept, RI is the refractive index at 20° C., d is the density in g/cm3 at 20° C. and 0.1 MPa, VGF is the viscosity gravity function, SG is the specific gravity at 15° C., and $\upsilon_{38}$ is the kinematic viscosity at 38° C. in mm²/s.

It is evident from experimental data that ASTM D86 distillation cannot account for the concentration of the components lighter than $C_5$ due to evaporation at room temperature during the experimental procedure, as well as sampling. The concentration of the light ends (n-butane and lighter) in naphtha is calculated using simple phase equilibrium calculations.

In this procedure, the RVP for the petroleum fraction (naphtha) is first obtained experimentally. Alternatively, the RVP may be estimated using the Riazi-Albahri equation (the below set of equations are collectively grouped as equation set (32)):

$$\text{RVP} = P_{cp}e^Y$$

$$Y = -X(T_b\text{SG}/T_r)(1-T_r)^5$$

$$X = -276.7445 + 0.06444T_b + 10.0245\text{SG} - 0.129T_b\text{SG} + 9968.8675/T_b\text{SG} + 44.6778 \ln(T_b) + 63.6683 \ln(\text{SG})$$

$$T_r = 311/T_{cp}$$

where $T_{cp}$ and $P_{cp}$ are the pseudo-critical temperature and pressure of the petroleum fraction in degrees Kelvin and bar, respectively. SG is the specific gravity at 15.5° C., RVP is in bars and $T_b$ is the normal boiling point in Kelvin.

The experimental or estimated RVP is converted into true vapor pressure (TVP) at 37.8° C. using the API method. The TVP is then used to calculate the concentration of the light ends in the naphtha using simple bubble (boiling) point calculations as:

$$\sum_{i=1}^{n} K'_i x_i = 1. \quad (33)$$

The vapor-liquid equilibrium constant (distribution coefficient) is simplified for ideal systems using Raoult's law as:

$$K'_i = \frac{P_i^v}{P_t} \quad (34)$$

where $P_i^v$ is the vapor pressure of the pure component i in the defined mixture, and $P_t$ is the true vapor pressure of the naphtha at 37.8° C.

Combining the above equations, the following simple relation is obtained:

$$\sum_{i=1}^{n} P_i^v x_i = P_t \quad (35)$$

which can be incorporated in the objective function of equations (21) and (22) and used to calculate the mole fraction of the light ends.

A multivariable optimization algorithm is used to minimize the objective function while calculating the concentration of the pure components. After calculating the objective function, the optimization technique alters the concentration until the minimum is found. This point represents the optimal concentrations that best fit the basic analytical data and quantitatively represents the naphtha sample.

Nearly all classical nonlinear optimizers are guaranteed only to find a locally optimal solution. To find a globally optimized solution, using, for example, the nonlinear GRG local optimization module, an alternative approach is typically used. The optimization program is run several times from judiciously chosen, but different, starting points, and the best solution found will be the best estimate of a globally optimized solution. Making use of this multi-start technique provides an estimate of the solution uniqueness.

In FIG. 4, steps 36-40 convert the pure component data (molecular description, physical properties, and calculated composition) into global properties (e.g., molecular weight and H/C content, etc.) using mixing rules at step 42. When molecular detail is available, it is possible to predict analytical results for multi-component mixtures through simple accounting or any other suitable methods for aggregating the molecules into lumped fractions. Molecular structure properties are computed by simply counting their occurrence with respect to composition. The averaged properties Θ are computed using weight, mole, or volume fractions as appropriate, where $f(\Theta i)$ may be the property of pure component i or a function thereof:

$$\Theta = \sum_{i=1}^{n} f(\Theta_i) x_i. \quad (36)$$

At steps 32 and 34, testing occurs. In order to verify the validity and accuracy of the MEPP model, the simulation outcome (in terms of average global properties of the petroleum fraction) are compared to those calculated using generalized correlations from the literature. A total of 30 naphtha samples were collected to assess model performance against experimental data and for error analysis. The experimental data cover a wide array of light and heavy petroleum naphtha, ranging in API gravity from 35 to 94, initial boiling point from 16.7 to 130.6° C. and final boiling point from 66.7 to 155.5° C.

The procedure used to test the model is as follows: The naphtha input to the model is characterized in terms of bulk properties (RVP, PNA, and ASTM D86 distillation). The MECM model is used to generate a molecular ensemble that retains the qualitative features expected to mimic the naphtha. The predicted molecular distributions are aggregated in the MEPP model to calculate the global properties (API, MW, viscosity, etc.). The model performance in simulating the actual petroleum fraction is compared to products from generalized correlations, which use the contemporary method of feed characterization. Error analyses are presented by comparing the global properties of the petroleum fraction obtained experimentally or predicted from experiment.

The ultimate output of the program is the global properties of light petroleum fractions from the knowledge of their conventional laboratory analysis, such as RVP, and PNA content, along with ASTM D86 distillation, with the latter being the minimum input required. Thus, when a petroleum naphtha sample is being tested for boiling point distillation, the other properties of the sample are also measured.

The accuracy of the method is verified by the validation model, the purpose of which is to crosscheck the method and validate its result by comparing its performance with other methods for determination of petroleum fractions global properties from the literature. The validation model includes methods for determination of global Properties of the petroleum fractions.

Figure 5:
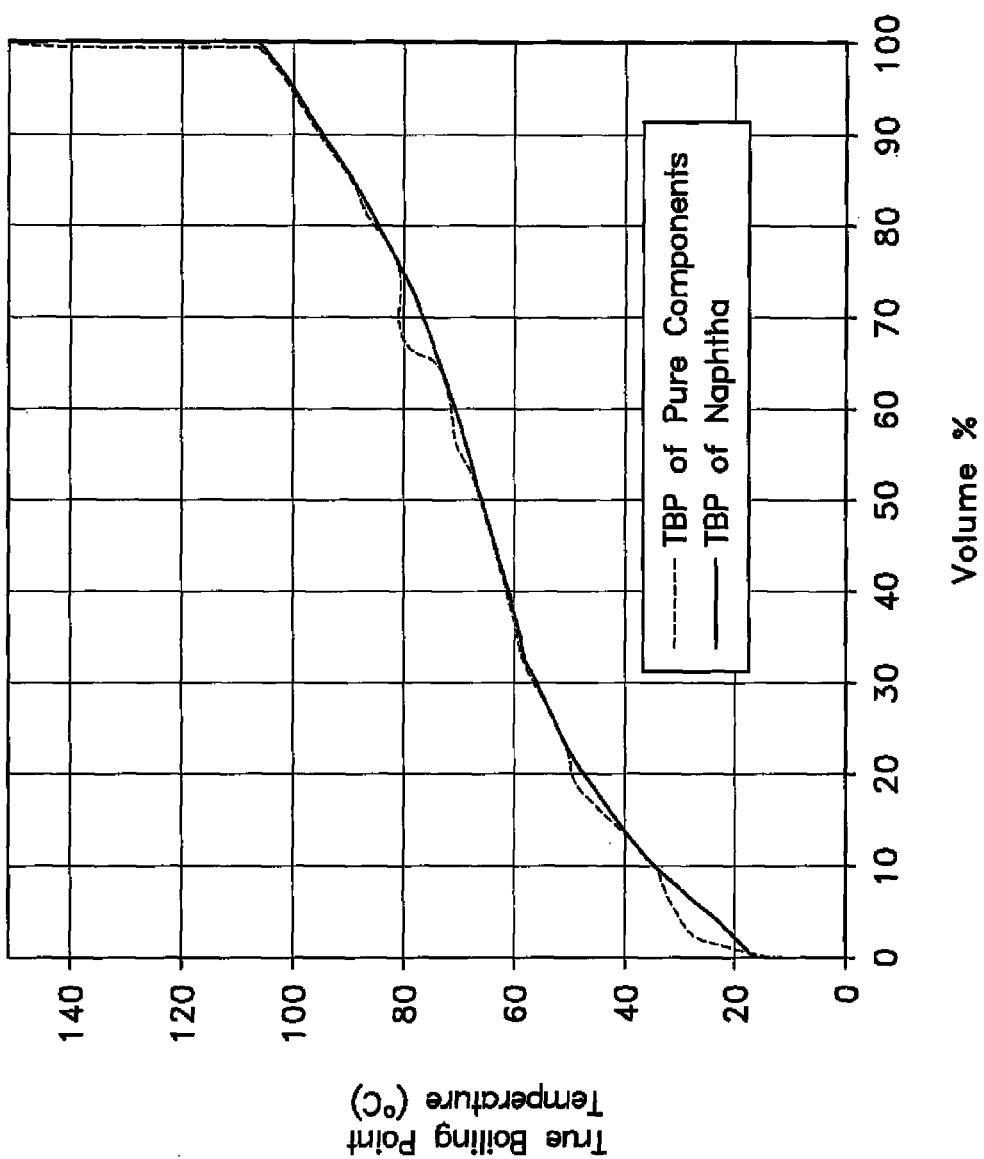
FIG. 5 is a graph illustrating a comparison between true boiling point temperature predicted by the present method for measuring the properties of petroleum fuels by distillation vs. experimental data.
Figure 6A:
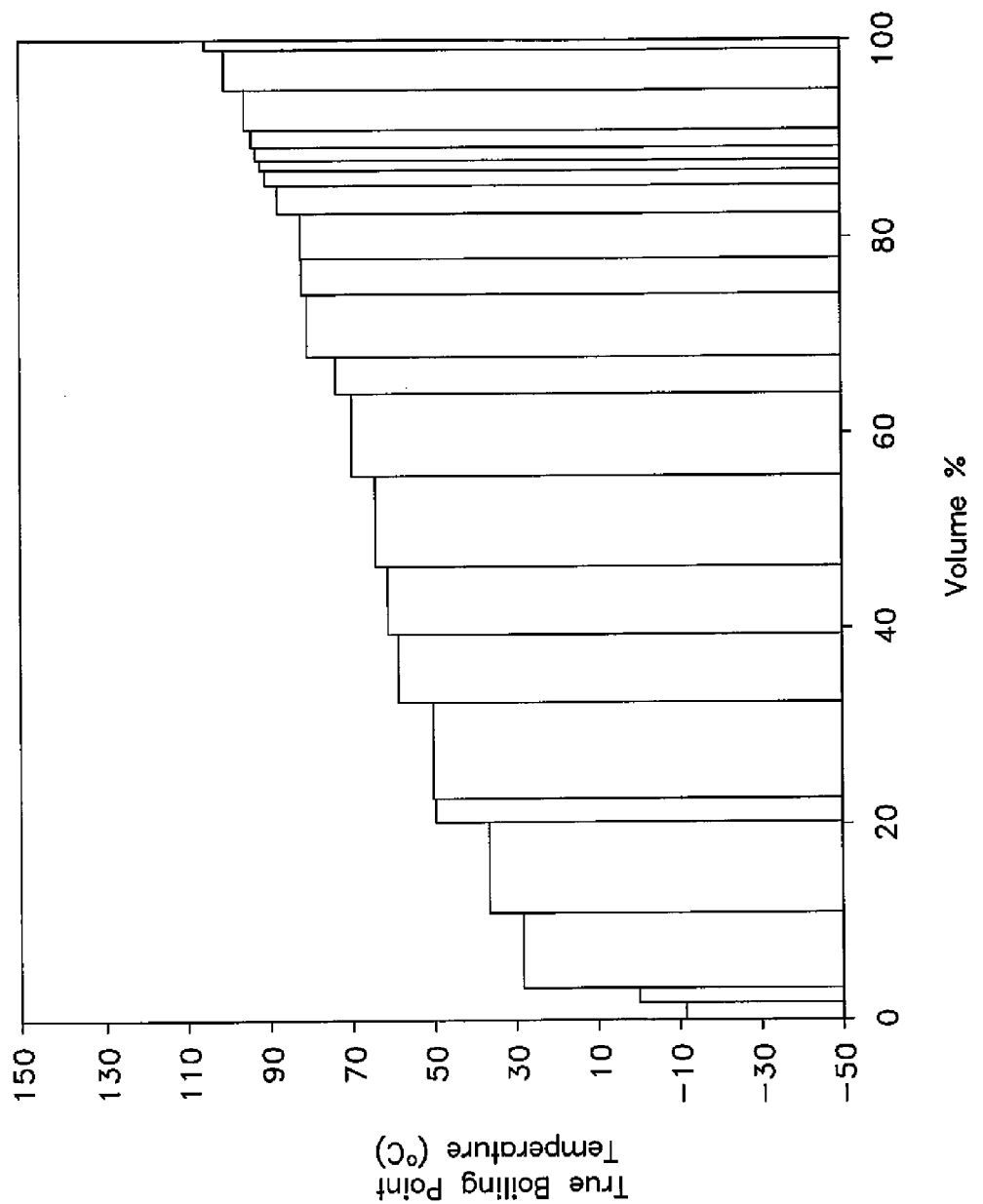
Figure 7D:
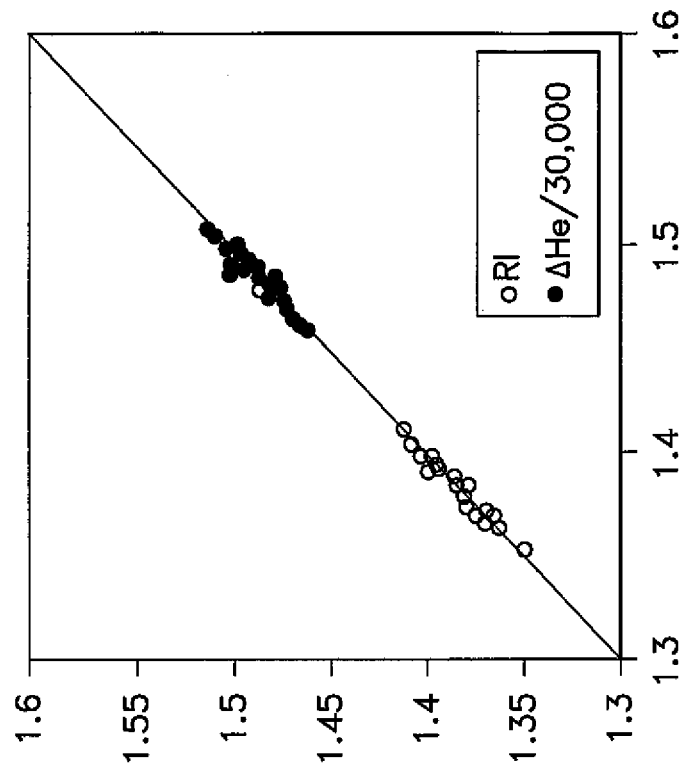
Figure 7C:
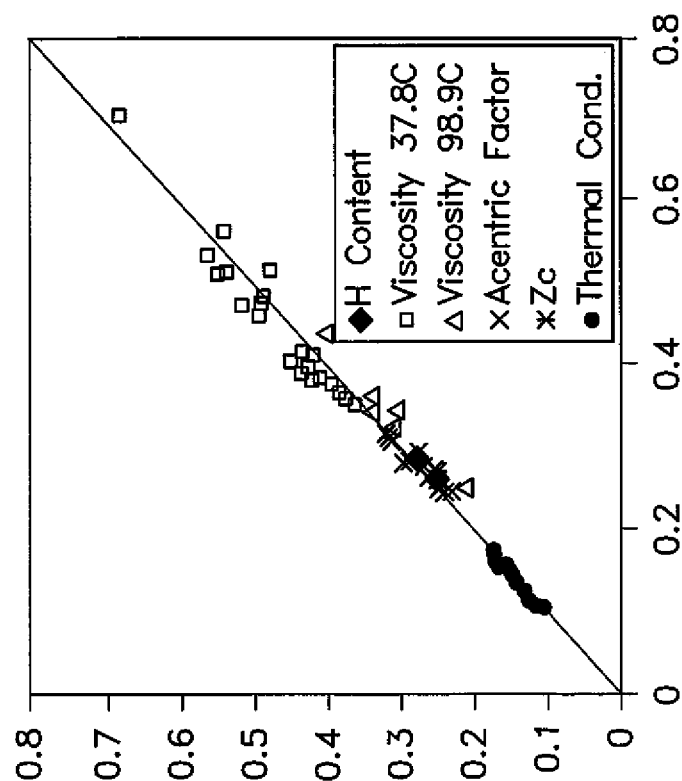
Figure 7F:
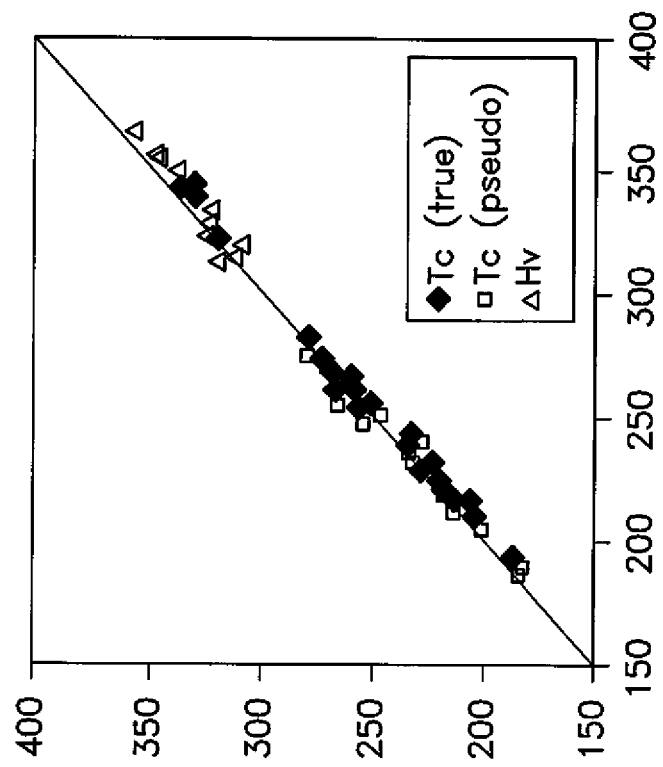
Figure 7E:
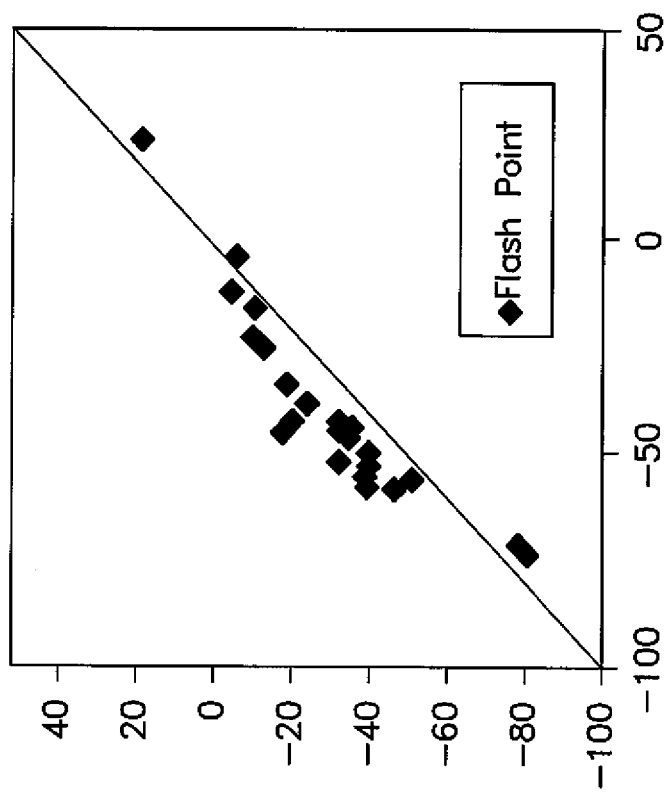

FIG. 5 illustrates a comparison of the overall experimentally measured boiling point distribution with that predicted from the MECM simulation for petroleum naphtha. The components results demonstrate an almost exact match with the TBP curve to within statistical errors. There is a small deviation due to optimization of other properties (RVP and PNA content) in addition to the boiling points. To illustrate the fine-grained molecular detail of the output, the molecular distribution for 68 species used to simulate a naphtha feed for one case is shown in FIG. 6.

Using the MEPP methods and correlations to determine the petroleum fractions global properties, the PNA compositions and physical properties of one of the samples (petroleum naphtha reformate fraction) are estimated and tabulated in Table 3. The same properties estimated from aggregation of the molecular ensemble for the MEPP simulated petroleum fraction are also shown in Table 3. The percent deviations of these estimated properties are also shown. The small deviations indicate how the MEPP estimated properties are representative of the undefined petroleum mixture.

Figure 8:
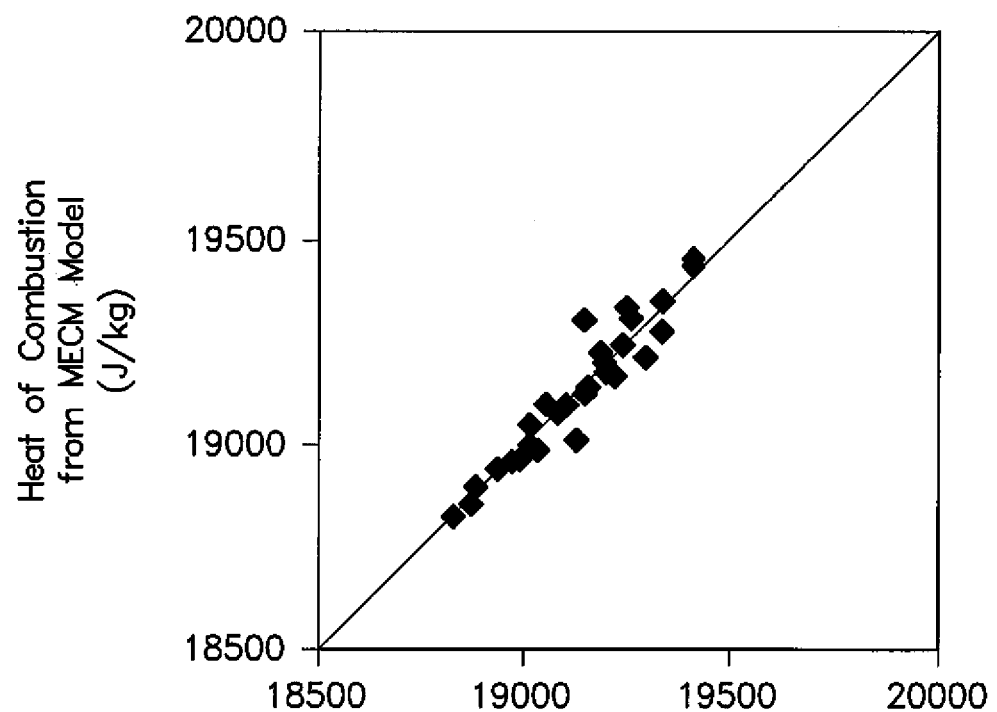
FIG. 8 is a parity diagram illustrating the net heat of combustion of petroleum naphtha, with the x-axis representing the net heat of combustion calculated via generalized correlations, and the y-axis representing the net heat of combustion calculated via the present method for measuring the properties of petroleum fuels by distillation.

Detailed comparison for some selected properties for all naphtha samples are shown in the summary presented in Table 3 and the parity diagrams of FIGS. 7 and 8. The fit between the experimental and simulation results, as shown by the average percentage errors and correlation coefficients, is quite good. The average absolute deviation for all the properties in Table 3 is about 3.5% and the average correlation coefficient is 0.96.

The RVP and PNA fractional composition results demonstrate an almost exact match to within statistical errors. From all the properties investigated, the true vapor pressure at 37.8° C., the specific (API) gravity, molecular weight, surface tension of liquid at 25° C., Watson characterization factor, refractive index, hydrogen content, kinematic viscosity at 37.8 and 98.9° C., true critical temperature, pseudo-critical temperature, pseudo-critical pressure, acentric factor, the liquid thermal conductivity at 25° C., flash point, net heat of combustion at 25° C., heat of vaporization at the normal boiling point, and the mean, cubic, weight, molar, and volume average boiling points correlated very well as evident by the average percentage errors and correlation coefficients that were in the upper nineties. Less accurate, but still efficient, predications were for the aniline point, motor octane number, and critical compressibility factor with correlation coefficients ranging between 0.8 and 0.9, and with average percentage errors of 5.38% or less.

A further example illustrates property prediction of the petroleum fractions using a pseudo-component method. In this method, the boiling point distribution, such as that obtained from the ASTM D86 distillation, for example, is first fitted to any form of algebraic equation, such as the probability density function (PDF) of equation (24), or a fourth-order polynomial function, such as equation (23). In the preferred embodiment, the fourth-order polynomial function is utilized. This is used to generate a multitude of boiling point values $T_{bi}$ at desired values of the samples volume % distilled.

The property of the petroleum fraction is calculated using the following equation:

$$\text{Property} = \Sigma(x_v)_i (\text{PVBI})_i \quad (37)$$

where i=1, 2, 3, . . . , n and $(x_v)_i$ is the volume fraction of the pseudo-component cut, n is the number of pseudo-component cuts, and $(\text{PVBI})_i$ is the property volume blending index of cut i given by the following quadratic equation:

$$(\text{PVBI})_i = a + b(T_b)i + c(T_b)i^2. \quad (38)$$

The property volume blending index could be the specific gravity, for example, with $(T_b)_i$ being the boiling point value from the ASTM D86 distillation curve corresponding to the mid-volume percent of the pseudo-component cut i.

Mole and weight blending indexes may also be used in equation (37) with the volume blending index being preferred. In that case, appropriate weight, mole, or volume fraction averaging or blending methods may be used. It should be understood that any suitable linear averaging methods of the volume, weight, or mole blending indexes may be used instead of the simple linear averaging. Non-linear averaging is also possible, either in terms of the mole, weight and volume fractions, or in terms of the weight, weight and volume blending indexes, or both.

For calculating the specific gravity of the petroleum fraction, for example, equation (38) is used to calculate the specific gravity volume blending index $(\text{SGVBI})_i$, where $T_{bi}$ is in degrees C., using the following constants determined by regression from experimental data and the least square method: a=0.640500305; b=0.000847828; and c=−4.84×10⁻⁷.

Figure 9:
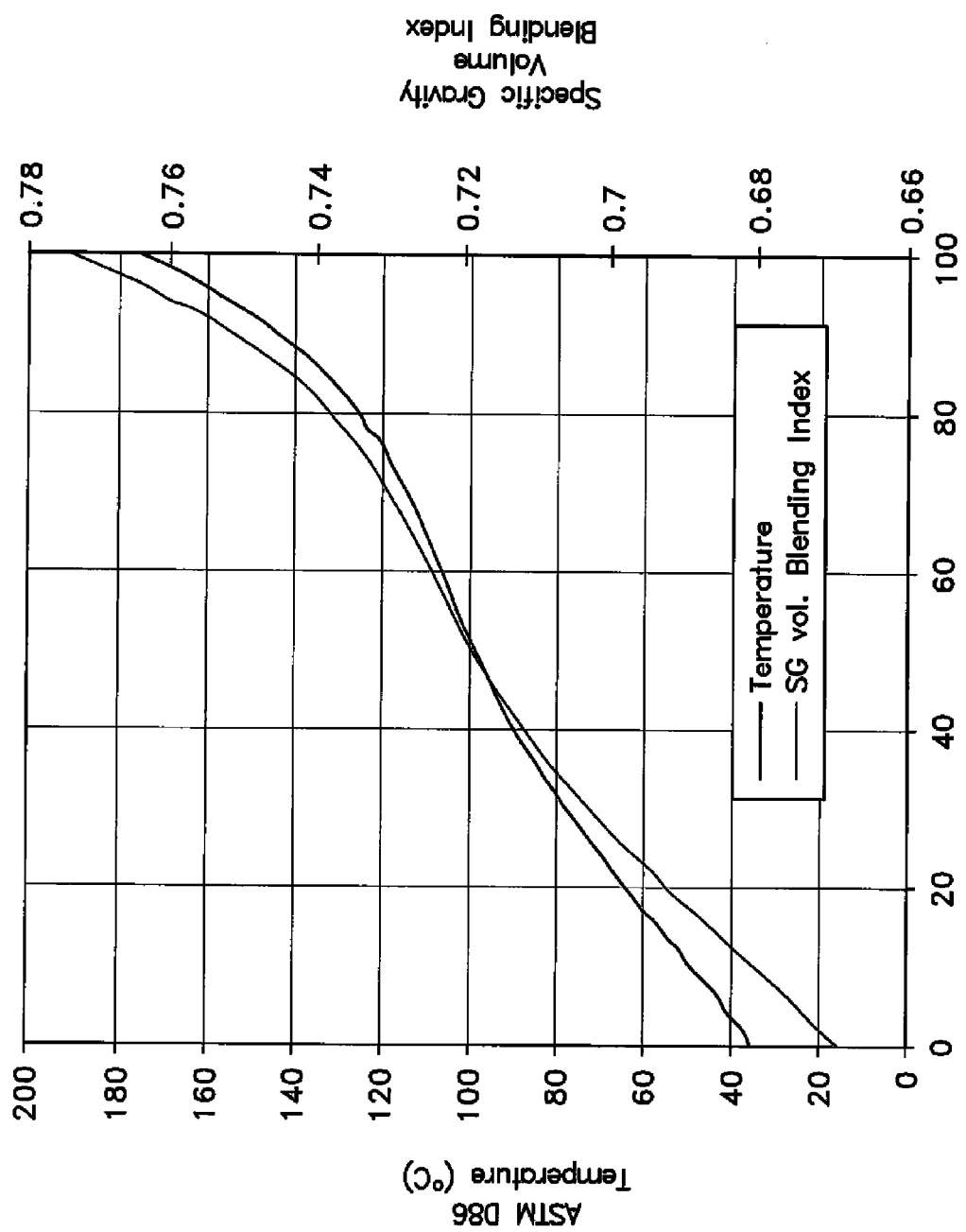
FIG. 9 illustrates ASTM D86 boiling point distribution and the specific gravity volume blending index distribution, calculated by the present method for measuring the properties of petroleum fuels by distillation.

The distribution of the specific gravity volume blending index $(\text{SGVBI})_i$ is shown with that of the ASTM D86 boiling point temperature in FIG. 9. A quadratic equation was effectively used to capture the distribution of the SG volume blending index. There was no need for a higher order polynomial function, since the constant for the third and fourth order parameters were evaluated by regression as zero.

Choosing 100 volume-based pseudo-components with a one volume % cut each $(x_{vi}=0.01)$, the specific gravity is calculated from equation (37) by simply volume-averaging the $(\text{SGVBI})_i$ for the 100 cuts at cumulative mid-volume % values of 0.5, 1.5, 2.5, . . . , 99.5 as follows:

$$\text{SG} = \Sigma(\text{SGVBI})_i \quad (39)$$

where i=1, 2, 3, . . . , 100.

Figure 10:
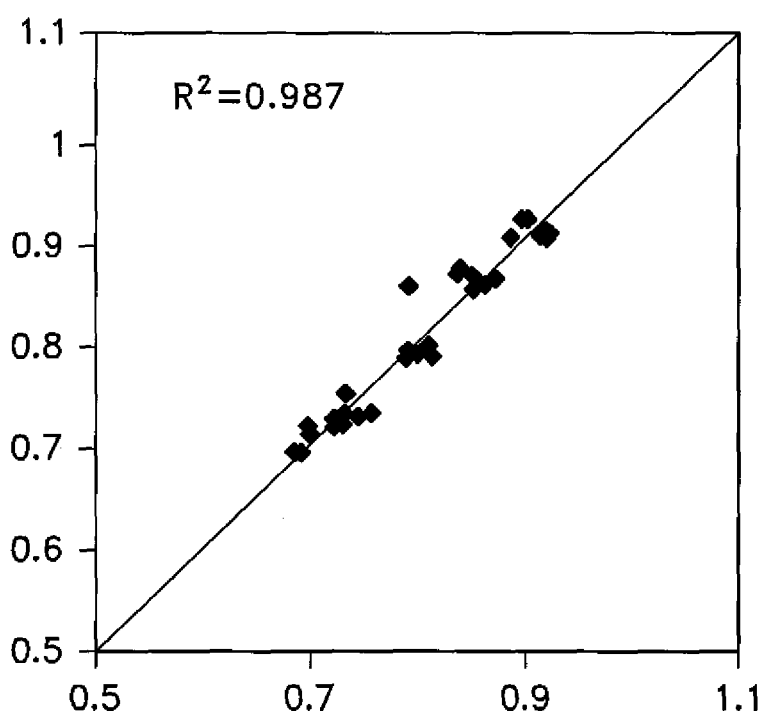
FIG. 10 is a parity diagram illustrating the specific gravity of 206 petroleum fractions, with the x-axis representing the specific gravity calculated via generalized correlations, and the y-axis representing the specific gravity calculated via the present method for measuring the properties of petroleum fuels by distillation.

FIG. 10 illustrates the a test of the above procedure to predict the SG of 206 petroleum fractions including naphtha, kerosene, diesel and heavy gas oil, with the boiling point ranging from 30 to 540° C. and API from 20 to 75, along with an SG from 0.6849 to 0.9248. FIG. 10 shows the predicted specific gravities for these petroleum fractions plotted against experimental data in a parity diagram with a correlation coefficient of 0.987. The average absolute deviation is 0.0091 and the absolute average percentage error is 1.12%, which is well within experimental error. The maximum deviation and error are 0.0647 and 8.16%, respectively.

It is possible to choose a lesser number of pseudo-components with equal volume % for each. For example, one may choose 50 pseudo-components with two volume percent each. Then, the volume index is calculated at cumulative mid-volume % values of 1, 3, 5, . . . , 99, etc. It is also possible to choose non-equal volume % for each pseudo-component.

The above pseudo-component model can be further simplified, assuming the whole petroleum fraction includes five volume-based pseudo-component cuts with 20 volume % each. The mid-volume boiling point of cut 1 is equal to the 10% distillation temperature $(T_{10})$. The mid-volume boiling point of cut 2 is equal to the 30% distillation temperature $(T_{30})$. The mid-volume boiling point of cut 3 is equal to the 50% distillation temperature $(T_{50})$. The mid-volume boiling point of cut 4 is equal to the 70% distillation temperature $(T_{70})$. The mid-volume boiling point of cut 5 is equal to the 90% distillation temperature $(T_{90})$. This conveniently ignores the IBP and FBP, since they are usually not as accurately determined as the other boiling point temperatures by the ASTM D86 distillation test.

In this case, the specific gravity is calculated from equation (37) by simply adding the volume weighted (averaged) $(\text{SGVBI})_i$ for the five pseudo-component cuts evaluated at the boiling point temperatures corresponding to the 10, 30, 50, 70, and 90 cumulative mid-volume percents as:

$$\text{SG} = \Sigma(x_v)_i (\text{SGVBI})_i \quad (40)$$

where i=20, 40, 60, 80, 100. SG is the specific gravity of the petroleum fraction, $(x_v)_i$ is the volume fraction of each pseudo-component which is 20%, or 0.2, weight fraction and $(\text{SGVBI})_i$ is the specific gravity volume blending index given by the following quadratic equation (obtained by regression from experimental data):

$$(\text{SGVBI})_i = 0.620810874 + 0.001038583(T_{bi}) - 8.94 \times 10^{-7}(T_{bi})^2 \quad (41)$$

where i=10, 30, 50, 70, 90 and $T_{bi}$ is the ASTM D86 boiling point temperature in degrees C. corresponding to 10, 30, 50, 70, and 90 volume % vaporization of the sample.

Calculating the $(\text{SGVBI})_i$ at 10, 30, 50, 70, 90 volume % temperatures and then substituting into equation (40), the final expression for the specific gravity of the petroleum fraction in terms of the ASTM D86 boiling point temperatures is given by the following expression with almost the same accuracy as the detailed model:

$$\text{SG} = 0.620810874 + 0.0002077166(T_{10} + T_{30} + T_{50} + T_{70} + T_{90}) - 1.788 \times 10^{-7}[(T_{10})^2 + (T_{30})^2 + (T_{50})^2 + (T_{70})^2 + (T_{90})^2]. \quad (42)$$

The predicted specific gravities for the above petroleum fractions are contrasted against experimental data with a correlation coefficient of 0.991, an average absolute deviation of 0.0038, and an absolute average percentage error 0.93%, which is well within experimental error and a maximum deviation and error of 0.0296 and 3.53%, respectively.

Equation (42) is useful when complete boiling point distribution is available and excessive computation is not desirable.

The above model can be further simplified by assuming the whole petroleum fraction as one pseudo-component cut with 100 volume % and a mid-volume boiling point equal to the 50% distillation temperature. Applying the above assumption reduces the entire model to the following single equation with almost the same accuracy as the detailed model:

$$SG = 0.61830388 + 0.001072356(T_{50}) - 9.68 \times 10^{-7}(T_{50})^2 \qquad (43)$$

where SG is the specific gravity of the petroleum fraction and $T_{50}$ is the ASTM D86 boiling point temperature in degrees C. corresponding to 50 volume % vaporization of the sample. This equation is useful when complete boiling point distribution is not available.

The predicted specific gravities for the above petroleum fractions using equation (43) compared against the experimental data with a correlation coefficient of 0.991, an average absolute deviation of 0.0033, and an absolute average percentage error 0.87%, which is well within experimental error and a maximum deviation and error of 0.0306 and 3.64%, respectively.

Although equations (42) and (43) are comparable in terms of average percentage error and correlation coefficient, the former is preferred when complete boiling point distribution is available. The above method can be applied to predict other properties of the petroleum fraction, such as the freezing point, the Reid vapor pressure, the molecular weight, and the like, and in particular to predict the mass, mole or volume specific properties such as enthalpy, heat capacity, molecular weight, heat of combustion, heat of vaporization by calculating through regression from appropriate experimental data the values of the constants of equation (38), a, b, and c, or any other appropriate equation including non-quadratic equations. The boiling point distribution may be the true boiling point distribution or any other suitable boiling point distribution obtainable from a distillation device, a gas chromatograph, or infrared spectroscopy or the like, since inter-conversion between these is well known.

As noted above, the property prediction of petroleum fractions may be accomplished using a neural network. An artificial intelligence system can be used with a conglomeration of boiling point distribution data to provide a method of improving recognition of an unknown from its boiling pattern. Customized neural network systems allow for optimized organization and resourceful use of variables already existing in the distillation apparatus, providing a much more comprehensive, discrete and accurate differentiation and matching of boiling point than is possible with human memory. This allows for increased speed of fingerprinting analysis, accuracy and reliability, together with a decreased learning curve and heightened objectivity for the analysis.

Characteristic boiling point distributions are obtained for the materials, via distillation techniques including ASTM D86, ASTM D1160, and the like. Desired portions of the boiling point distribution may be selected and then placed in proper form and format for presentation to a number of input layer neurons in an offline neural network. The network is first trained according to a predetermined training process, and it may then be employed to identify the properties of particular materials in situ or in real time.

The usage of such a neural network in system 10 is particularly useful for recognizing and identifying organic compounds, such as complex hydrocarbons, whose properties conventionally require a high level of training and many hours of hard work to identify, and are frequently indistinguishable from one another by human interpretation.

Figure 11:
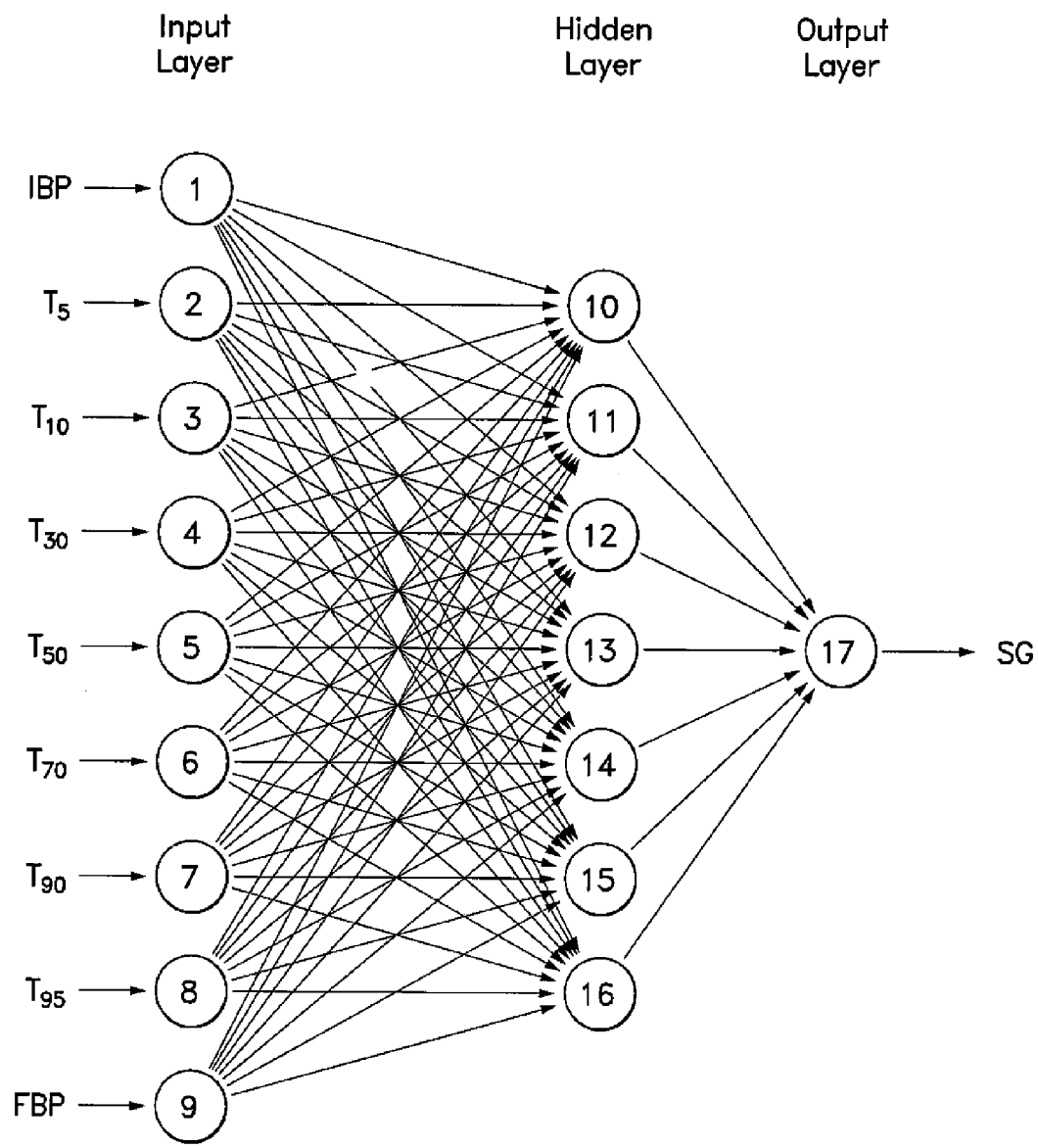
FIG. 11 diagrammatically illustrates a neural network architecture for predicting the specific gravity of petroleum fractions according to the present invention.

Using the back-propagation neural network architecture shown in FIG. 11 with an input layer consisting of nine neurons, representing the boiling point temperatures obtained from distillation, and one hidden layer consisting of seven neurons with the sigmoid transfer function. The specific gravity of the 176 petroleum fractions in the earlier example were used to train the network and 30 were used to test the trained network.

Figure 12:
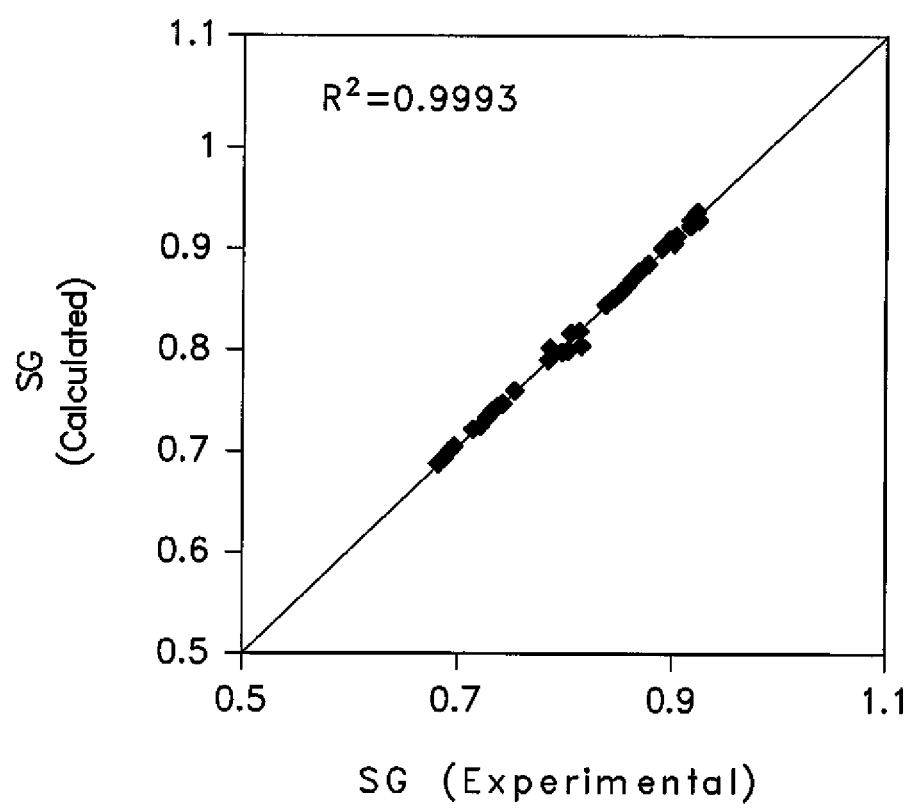
FIG. 12 is a parity diagram illustrating the specific gravity of 206 petroleum fractions using the neural network architecture of FIG. 11, with the x-axis representing the specific gravity calculated via generalized correlations, and the y-axis representing the specific gravity calculated via the present method for measuring the properties of petroleum fuels by distillation.

The predicted specific gravities for these petroleum fractions is plotted against experimental data in the parity diagram of FIG. 12 with an overall correlation coefficient of 0.9993 (for the combined training and testing sets) and an overall absolute average percentage error 0.172%, with a maximum error of 1.71%, showing high accuracy.

The above procedure can be applied to other properties of the petroleum fraction, such as the freezing point, the Reid vapor pressure, the molecular weight, and the like by training the neural networks from appropriate experimental data. The boiling point distribution may be the true boiling point distribution or any other suitable boiling point distribution obtainable from a distillation device, a gas chromatograph, or infrared spectroscopy or the like, since Inter-conversion between these is well known.

The input layer mainly includes the boiling point distribution obtained above. The boiling point distribution input to the network may include approximate boiling point temperatures, as desired, with the minimum being the 50 volume % boiling point temperature. The input layer may additionally include other parameters to compensate for the presence of additives or property boosters (such as RVP to compensate for the normal-butane and normal and isopentane addition as an octane number enhancer) or SG or inherent structural information (such as the PNA or PIONA or ASO composition).

Figure 13:
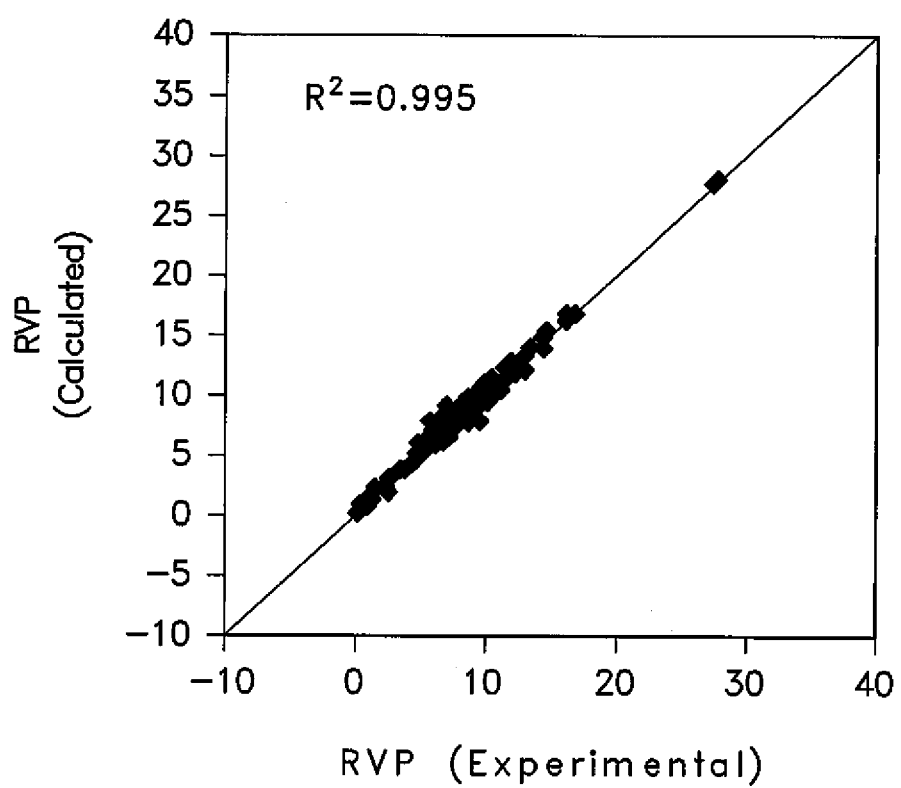
FIG. 13 is a parity diagram illustrating the RVP of 362 petroleum fractions using the neural network architecture of FIG. 11, with the x-axis representing the RVP calculated via generalized correlations, and the y-axis representing the RVP calculated via the present method for measuring the properties of petroleum fuels by distillation.

Additionally, the network architecture of the previous example was used to predict the RVP of petroleum fractions using 20 neurons in the hidden layer and the same seven neurons in the input layer, which included the ASTM D86 boiling point temperatures at several volume % distilled. 70% of the total 362 experimental samples were used to train the neural networks, while the remaining 30% were used to test the trained network. Model predictions for RVP were in excellent agreement with the experimental data. The overall correlation coefficient was 0.995 for the combined training and testing sets, as shown in the parity diagram in FIG. 13. The overall average deviation was 0.3186 psi and the overall maximum deviation was 2.0 psi, which is well within the experimental accuracy. The RVP ranged from 0.1 to 66 psi, and boiling point ranged from 17 to 500° C.

Further, several neural network architectures were investigated for their ability to predict the research octane number of gasoline. The network architecture of the previous examples was used to predict the RON of gasoline using 18 neurons in the hidden layer and the same input parameters as in that example, including only the ASTM D86 boiling point data. 70% of the data was used to train the neural networks, while the remaining 30% were used to test the trained network. Model predictions for RON were in moderate agreement with experimental data with an overall correlation coefficient was 0.90. For the combined training and testing sets, consisting of 333 experimental samples, the overall average deviation was 2.8 and the overall maximum deviation was 31. The RON ranged from 34 to 107 and boiling point ranged from 17 to 500° C. The parity diagram for the model's predictions is shown in FIG. 14A.

In an effort to improve the models' predictions, several other network architectures were investigated for their ability to predict RON, using such input parameters as Reid vapor pressure (RVP) and aromatic, olefin, and saturate fractional composition (AOS), in addition to the ASTM D86 boiling point temperatures. A summary of the models' predictions is shown in Table 5 below:

TABLE 5

| Input parameters | # of neurons in hidden layers | Average % Error | Max. % Error | Correlation Coefficient |
|---|---|---|---|---|
| Boiling point | 18 | 2.8 | 31.2 | 0.90 |
| Boiling point + RVP | 16 | 2.5 | 26.8 | 0.927 |
| Boiling point + AOS | 7 | 2.2 | 22.7 | 0.95 |
| Boiling point + RVP + AOS | 7 | 1.12 | 8.2 | 0.995 |

Figure 15:
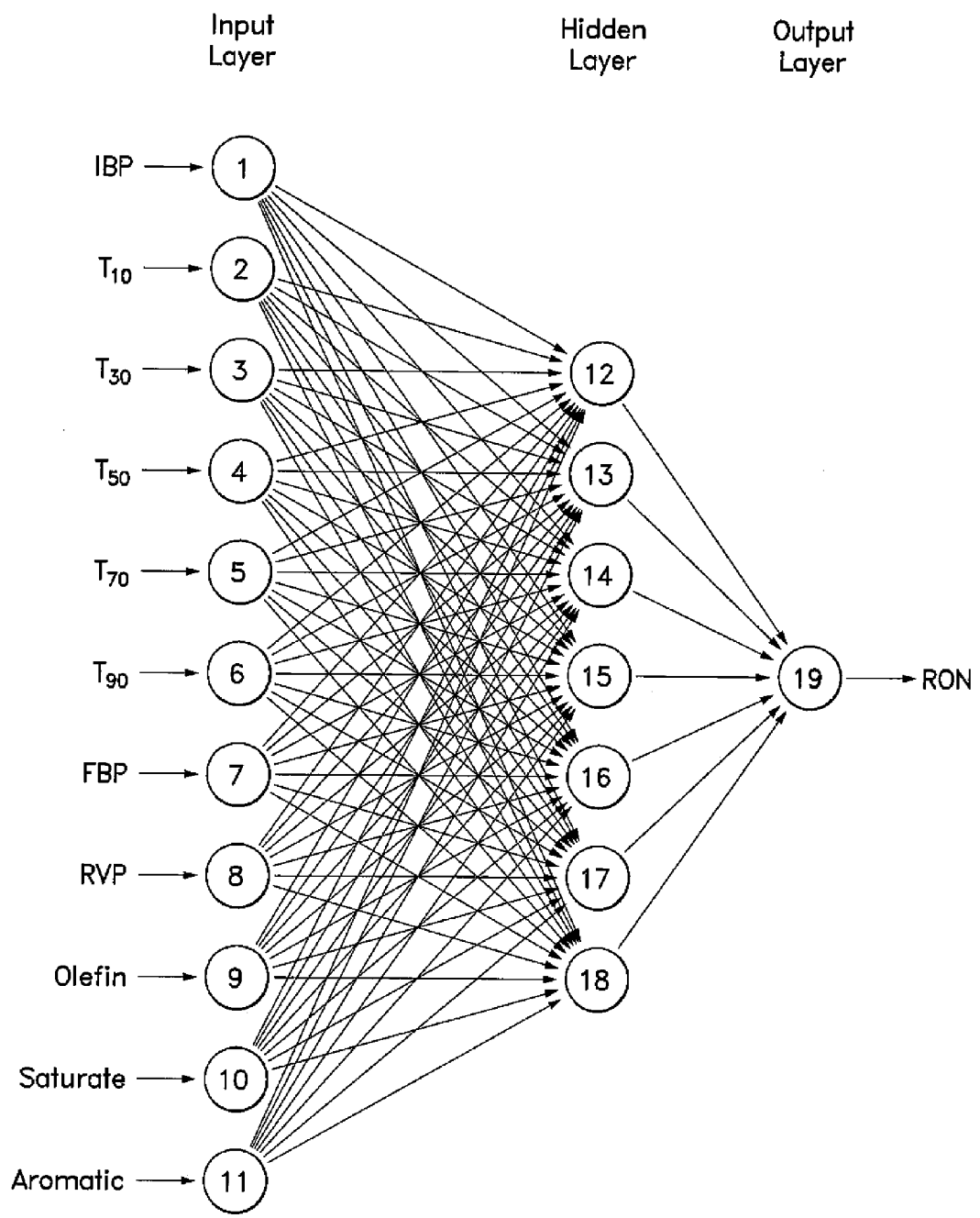
FIG. 15 diagrammatically illustrates a neural network architecture for predicting the RON of gasoline according to the present invention.

Best results are obtained from the neural network architecture shown in FIG. 15, consisting of 7 neurons in the hidden layer and 11 neurons in the input layer, including the ASTM D86 boiling point temperatures at several volume % distilled in addition to the RVP and the aromatic, olefin, and saturate fractional composition (AOS), with an overall average % error of 1.12 and correlation coefficient of 0.995. The parity diagrams for all cases are shown in FIGS. 14A, 14B, 14C and 14D.

The present method may be used to predict a wide range of chemical and physical properties (including performance and perceptual properties) of petroleum fuels, such as, for example, molecular weight, true vapor pressure, the specific (API) gravity, various types of boiling point averages, Watson characterization factor ($K_w$), refractive index, carbon to hydrogen content, kinematic viscosity, the surface tension of liquid, aniline point, cloud point, true critical temperature, pseudo-critical temperature, true critical pressure, pseudo-critical pressure, critical compressibility factor, acentric factor, flash point, freezing point, heat of vaporization at the normal boiling point, net heat of combustion, isobaric liquid heat capacity, isobaric vapor heat capacity, liquid thermal conductivity, and research and motor octane numbers. Fuel properties may easily determined and displayed to the user, such as octane rating equivalent to the ASTM rating, molecular weight, and various other properties of the components of interest. The method may also be used in the recognition and identification of organic compounds, such as complex hydrocarbons, whose analysis conventionally requires a high level of training and many hours of hard work to identify.

In the preferred embodiment, the present method includes the following steps: (a) distilling a selected light petroleum fraction to determine at least the true boiling point thereof; (b) storing an initial data set of properties associated with the selected light petroleum fraction in computer readable memory, the initial data set of properties including API gravity, RVP, PNA content and the true boiling point; (c) generating a molecular ensemble including a plurality of molecular species, each with a known pure component API gravity, RVP, PNA content and true boiling point, and storing a pure component data set in the computer readable memory; (d) applying at least one mixing rule to the pure component data set to calculate a concentration of light components of the selected light petroleum fraction based upon the pure component API gravity and RVP; (e) applying the at least one mixing rule to the pure component data set to calculate a concentration of heavier components of the selected light petroleum fraction based upon the pure component PNA content and true boiling point; (f) comparing the API gravity, the RVP, the PNA content and the true boiling point of the initial data set with the pure component API gravity, RVP, PNA content and true boiling point to form a set of comparison data; (g) optimizing the set of comparison data, the step of optimization including application of an objective function; (h) generating a set of component concentration data based upon the optimized comparison data; and (i) displaying the set of component concentration data.

In the above, the step of generating the molecular ensemble preferably includes generation of a molecular distribution of the pure components consisting of paraffins, olefins and aromatics. Optimizing the set of comparison data preferably includes minimizing a difference between the true boiling points of the pure components with the true boiling points of the initial data set. The minimization of the difference between the true boiling points of the pure components with the true boiling points of the initial data set preferably is performed by varying concentration values associated with the pure components. The optimization may further include minimizing a difference between the RVP of the pure components with the RVP of the initial data set.

Generating the molecular distribution includes a calculation method such as optimization, multivariate regression, partial least square regression, principal component regression, topological optimization, genetic algorithms, use of a neural network, and combinations thereof. The step of storing the initial data set of properties preferably includes storing estimated values for the API gravity, the RVP and the PNA content. The true boiling point of the selected light petroleum fraction is preferably found experimentally by ASTM D86 distillation, with the estimated values for the API gravity, the RVP and the PNA content being calculated based upon the true boiling point. Generation of a distribution of the molecular ensemble in terms of volume fractions by minimizing the objective function S is preferably accomplished as:

$$S = \sum_{j=1}^{n} ((Tb_j - T'b_j) \times W_o \times 100/Tb_j)^2 + ((PNA - PNA') \times W_1 \times 100/PNA)^2,$$

wherein j is an index number of the molecule and n represents the total number of molecules, PNA represents the paraffin, naphthene, and aromatic content for the petroleum fraction, PNA' is the paraffin, naphthene, and aromatic content for the petroleum fraction calculated from aggregating pure components in the molecular ensemble using the at least one mixing rule, $T'b_j$ is the boiling point of pure component j, $Tb_j$ is the boiling point value on a petroleum fractions true boiling point curve corresponding to component j, $W_0$ is a weighting factor for the boiling points and $W_1$ is a weighting factor for the PNA fractional composition.

Alternatively, the objective function S may be calculated as:

$$S = \sum_{j=1}^{n} ((Tb_j - T'b_j) \times W_o \times 100/Tb_j)^2 +$$
$$((P\% - P\%') \times W_1 \times 100/P\%)^2 +$$
$$((N\% - N\%') \times W_1 \times 100/N\%)^2 +$$
$$((A\% - A'\%) \times W_1 \times 100/A\%)^2,$$

-continued $$\text{wherein } P'^v = \sum_{i=1}^{n} P_i^v; P' \% = \sum_{i=1}^{n} P \%_i = \sum_{i=1}^{n} x_i^P;$$

$$N' \% = \sum_{i=1}^{n} N \%_i = \sum_{i=1}^{n} x_i^N; \text{ and } A' \% = \sum_{i=1}^{n} A \%_i = \sum_{i=1}^{n} x_i^A,$$

where $x_i$ is the mole fraction of pure component i, P %, N %, A % represent mole percent of paraffin, naphthene, and aromatic content, respectively, in the petroleum fraction, P'%, N'%, A'% represent the paraffin, naphthene, and aromatic contents, respectively, for the petroleum fraction calculated from aggregating pure components in the molecular ensemble using the at least one mixing rule, $P^v$ is the true vapor pressure of the petroleum fraction, and $P'^v$ is the true vapor pressure of the petroleum fraction, calculated from aggregation of pure components in the molecular ensemble.

The above is governed by the constraints $\Sigma x_i = 1$ and $\forall x_i \geq 0$. Alternatively, the method may include the following steps: (a) distilling a selected light petroleum fraction to determine a boiling point distribution of components of the selected light petroleum fraction; (b) storing an initial data set representing the boiling point distribution of the selected light petroleum fraction in computer readable memory; (c) dividing the selected light petroleum fraction into a predefined number of pseudo-components having equal volume fractions and assigning an average boiling point for each pseudo-component matching the boiling point value from the boiling point distribution; (d) calculating property-volume-blending-index values for the pseudo-components and correlating the calculated property-volume-index values to an average boiling point of the pseudo-components; and (e) aggregating the property-volume-blending-index values for the pseudo-components by applying at least one mixing rule to calculate at least one property associated with the selected light petroleum fraction as a function of the boiling point distribution.

In the above, the step of calculating the at least one property includes calculating a property value as Property=$\Sigma(x_v)_i$ (PVBI)$_i$, where Property represents the property value, i represents a particular pseudo-component cut where i=1, 2, 3, ..., n, with n representing the number of pseudo-component cuts, $(x_v)_i$ represents the volume fraction of the pseudo-component cut, and (PVBI)$_i$ represents the property volume blending index of cut i.

(PVBI)$_i$ is given by (PVBI)$_i$=a+b(T$_b$)i+c(T$_b$)i$^2$, where T$_b$ represents the boiling point of cut i, and coefficients a, b and c are based upon the correlation of the calculated property-volume-blending-index values to the average boiling point of the pseudo-components.

It is to be understood that the present invention is not limited to the embodiment described above, but encompasses any and all embodiments within the scope of the following claims.

I claim:

1. A method for measuring the properties of petroleum fuels by distillation using boiling point distribution, comprising the steps of:

distilling a selected light petroleum fraction to determine a boiling point distribution of components of the selected light petroleum fraction;

storing an initial data set representing the boiling point distribution of the selected light petroleum fraction in computer readable memory;

dividing the selected light petroleum fraction into a predefined number of pseudo-components having equal volume fractions and assigning an average boiling point for each pseudo-component matching the boiling point value from the boiling point distribution;

calculating property-volume-blending-index values for the pseudo-components and correlating the calculated property-volume-index values to an average boiling point of the pseudo-components, wherein the calculation includes calculating a property value as Property= $\Sigma(x_v)_i$(PVBI)$_i$, wherein Property represents the property value, i represents a particular pseudo-component cut where i=1, 2, 3, ..., n, with n representing the number of pseudo-component cuts, $(x_v)_i$ represents the volume fraction of the pseudo-component cut, and (PVBI)$_i$ represents the property volume blending represents index of cut i, further wherein (PVBI)$_i$ is given by (PVBI)$_i$=a+b(T$_b$)i+c(T$_b$)i$^2$, wherein T$_b$ represents the boiling point of cut i, and coefficients a, b and c are based upon the correlation of the calculated property-volume-blending-index values to the average boiling point of the pseudo-components;

aggregating the property-volume-blending-index values for the pseudo-components by applying at least one mixing rule to calculate at least one property associated with the selected light petroleum fraction as a function of the boiling point distribution, optimizing the property-volume-blending-index values;

generating a set of component concentration data based upon the optimized property-volume-blending-index values; and displaying the set of component concentration data.

* * * * *